US011874413B2

(12) United States Patent
Wu et al.

(10) Patent No.: US 11,874,413 B2
(45) Date of Patent: Jan. 16, 2024

(54) SYSTEMS FOR PET IMAGING

(71) Applicant: SHANGHAI UNITED IMAGING HEALTHCARE CO., LTD., Shanghai (CN)

(72) Inventors: Guanghe Wu, Shanghai (CN); Weiping Liu, Shanghai (CN); Shigang Su, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

(21) Appl. No.: 17/811,870

(22) Filed: Jul. 11, 2022

(65) Prior Publication Data
US 2022/0342096 A1 Oct. 27, 2022

Related U.S. Application Data

(60) Continuation of application No. 17/013,821, filed on Sep. 7, 2020, now Pat. No. 11,385,363, which is a
(Continued)

(30) Foreign Application Priority Data

Sep. 30, 2016 (CN) .......................... 201610874155.7
Oct. 14, 2016 (CN) .......................... 201610899032.9
(Continued)

(51) Int. Cl.
*G01T 1/29* (2006.01)
*A61B 6/03* (2006.01)
(Continued)

(52) U.S. Cl.
CPC ............ *G01T 1/2985* (2013.01); *A61B 6/032* (2013.01); *A61B 6/035* (2013.01); *A61B 6/037* (2013.01);
(Continued)

(58) Field of Classification Search
CPC ....... A61B 5/0035; A61B 5/032; A61B 5/035; A61B 5/037; A61B 5/4488; A61B 5/5235; G01R 33/481; G01T 1/2985
See application file for complete search history.

(56) References Cited

U.S. PATENT DOCUMENTS

2002/0020238 A1  2/2002  Takahashi et al.
2003/0063957 A1  4/2003  Hirabayashi
(Continued)

FOREIGN PATENT DOCUMENTS

CN     2305257 Y     1/1999
CN     2320364 Y     5/1999
(Continued)

OTHER PUBLICATIONS

First Office Action in Chinese Application No. 201611256679.6 dated Nov. 16, 2017, 12 pages.
(Continued)

*Primary Examiner* — Mark R Gaworecki
(74) *Attorney, Agent, or Firm* — METIS IP LLC

(57) ABSTRACT

The present disclosure relates to a system for PET imaging. The system may include a first device and a second device. The first device may include a first scanning channel. The second device may include a second scanning channel connected to the first scanning channel, a heat generating component, and a cooling assembly configured to cool the heat generating component, wherein the cooling assembly may include an inlet chamber and a return chamber, the heat generating component may be closer to a first side of the second device than at least one of the inlet chamber or the return chamber, and the first side of the second device may face the first device.

19 Claims, 28 Drawing Sheets

Related U.S. Application Data continuation of application No. 16/371,185, filed on Apr. 1, 2019, now Pat. No. 10,768,319, which is a division of application No. 15/721,776, filed on Sep. 30, 2017, now Pat. No. 10,267,930.

(30) Foreign Application Priority Data

| Oct. 14, 2016 | (CN) | ......................... 201621125553.0 |
| Nov. 15, 2016 | (CN) | ......................... 201611032775.2 |
| Nov. 25, 2016 | (CN) | ......................... 201621280709.2 |
| Nov. 30, 2016 | (CN) | ......................... 201611086609.0 |
| Dec. 30, 2016 | (CN) | ......................... 201611256679.6 |

(51) Int. Cl.
    *A61B 6/00*     (2006.01)
    *G01R 33/48*     (2006.01)
    *A61B 5/00*     (2006.01)

(52) U.S. Cl.
    CPC .......... *A61B 6/4488* (2013.01); *A61B 6/5235* (2013.01); *A61B 5/0035* (2013.01); *G01R 33/481* (2013.01)

(56) References Cited

U.S. PATENT DOCUMENTS

| 2004/0114723 | A1 | 6/2004 | Ray et al. |
| 2005/0135560 | A1* | 6/2005 | Dafni ................. A61B 6/56 378/101 |
| 2007/0242804 | A1 | 10/2007 | Vogtmeier et al. |
| 2007/0280410 | A1 | 12/2007 | Lutz et al. |
| 2007/0284535 | A1 | 12/2007 | Heismann et al. |
| 2009/0079430 | A1 | 3/2009 | Yamashita |
| 2010/0188082 | A1 | 7/2010 | Morich et al. |
| 2012/0018644 | A1 | 1/2012 | Caruba |
| 2013/0119259 | A1 | 5/2013 | Martin |
| 2015/0208991 | A1* | 7/2015 | Stoutenburgh ....... A61B 6/0442 378/209 |
| 2015/0272525 | A1 | 10/2015 | Kühn et al. |
| 2016/0067525 | A1 | 3/2016 | Bouchet et al. |
| 2016/0187496 | A1 | 6/2016 | Bradford et al. |
| 2017/0059720 | A1 | 3/2017 | Mcbroom et al. |
| 2017/0168169 | A1* | 6/2017 | Liu ................. G01T 1/2985 |
| 2017/0176607 | A1 | 6/2017 | Liu et al. |
| 2018/0231673 | A1 | 8/2018 | Yan et al. |

FOREIGN PATENT DOCUMENTS

| CN | 101061955 | A | 10/2007 | |
| CN | 201159224 | Y | 12/2008 | |
| CN | 202132505 | U | 2/2012 | |
| CN | 203062441 | U | 7/2013 | |
| CN | 203138519 | U | 8/2013 | |
| CN | 103479372 | A | 1/2014 | |
| CN | 103860187 | A | 6/2014 | |
| CN | 104367332 | A | 2/2015 | |
| CN | 104382609 | A | 3/2015 | |
| CN | 104765121 | A | 7/2015 | |
| CN | 104825181 | A | 8/2015 | |
| CN | 104825184 | A | 8/2015 | |
| CN | 104985447 | A | 10/2015 | |
| CN | 105140872 | A | 12/2015 | |
| CN | 205198010 | U | 5/2016 | |
| CN | 105769230 | A | 7/2016 | |
| CN | 105943072 | A | 9/2016 | |
| CN | 106137236 | A | 11/2016 | |
| CN | 106333703 | A | 1/2017 | |
| JP | H09197048 | A | 7/1997 | |
| JP | 2001009651 | A | 1/2001 | |
| JP | 2003028115 | A | 1/2003 | |
| JP | 2003056518 | A | 2/2003 | |
| JP | 2010099396 | A | 5/2010 | |
| WO | WO-2014080083 | A1 * | 5/2014 | ............. A61B 6/032 |
| WO | 2015142499 | A1 | 9/2015 | |

OTHER PUBLICATIONS

First Office Action in Chinese Application No. 201610899032.9 dated Oct. 29, 2018, 7 pages.
First Office Action in Chinese Application No. 201621125553.0 dated Jun. 20, 2017, 3 pages.
First Office Action in Chinese Application No. 201611032775.2 dated Feb. 1, 2019, 15 pages.
The Second Office Action in Chinese Application No. 201610899032.9 dated May 23, 2019, 20 pages.
The Fourth Office Action in Chinese Application No. 201610874155.7 dated Aug. 18, 2020, 16 pages.
First Office Action in Chinese Application No. 201710075118.4 dated Mar. 21, 2019, 14 pages.

\* cited by examiner

SYSTEMS FOR PET IMAGING

CROSS-REFERENCE TO RELATED APPLICATIONS

This application is a continuation of U.S. patent application Ser. No. 17/013,821, filed on Sep. 7, 2020, which is a continuation of U.S. patent application Ser. No. 16/371,185, filed on Apr. 1, 2019, now issued U.S. Pat. No. 10,768,319, which is a division of U.S. patent application Ser. No. 15/721,776, filed on Sep. 30, 2017, now issued U.S. Pat. No. 10,267,930, which in turn claims priority of Chinese Patent Application No. 201610874155.7 filed on Sep. 30, 2016, Chinese Patent Application No. 201610899032.9 filed on Oct. 14, 2016, Chinese Application No. 201621125553.0 filed on Oct. 14, 2016, Chinese Application No. 201611032775.2 filed on Nov. 15, 2016, Chinese Application No. 201621280709.2 filed on Nov. 25, 2016, Chinese Application No. 201611086609.0 filed on Nov. 30, 2016, and Chinese Patent Application No. 201611256679.6 filed on Dec. 30, 2016, the entire contents of each of which are hereby incorporated by reference.

TECHNICAL FIELD

This present disclosure relates to an imaging system, and more particularly, relates to a positron emission tomography (PET) imaging system and a positron emission tomography-computed tomography (PET-CT) imaging system.

BACKGROUND

Positron emission computed tomography (PET) is a nuclear medicine functional imaging technique that is used to observe metabolic activities in a subject. A PET system has multiple components including a gantry assembly, a detector assembly, a cooling assembly, etc. Proper installation, maintenance, and protection of the multiple components may affect various aspects of performance of a PET system including, e.g., the imaging accuracy, service life, work efficiency, etc. It is desirable to improve the design of multiple components to facilitate the installation, maintenance, and protection of the PET system. Besides, a subject needs to be exposed to radiation in PET-CT imaging. Thus, it is desirable to improve the design of the PET-CT imaging system to reduce the radiation dose.

SUMMARY

One aspect of the present disclosure relates to a system for imaging. The system may include a first device and a second device. The first device may include a first scanning channel. The second device may include a second scanning channel connected to the first scanning channel, a heat generating component, and a cooling assembly configured to cool the heat generating component, wherein the cooling assembly may include an inlet chamber and a return chamber, the heat generating component may be closer to a first side of the second device than at least one of the inlet chamber or the return chamber, and the first side of the second device may face the first device.

Another aspect of the present disclosure relates to a system for imaging. The system may include a detector assembly, a gantry assembly, and a cooling assembly. The detector assembly may include a plurality of detector modules. The gantry assembly may include a main gantry and a gantry base, wherein the gantry base may be configured to support the main gantry, and the detector assembly may be mounted on the main gantry. The cooling assembly may include a cooler, a chilling chamber surrounding the plurality of detector modules, an inlet chamber, and a return chamber, wherein the inlet chamber may be in fluid communication with the chilling chamber, the return chamber may be in fluid connection with the cooler, the inlet chamber and the return chamber may have a common plane, and the common plane may include a first thermal insulation layer.

A further aspect of the present disclosure relates to a system for imaging. The system may include a gantry assembly, a heat generating component mounted on the main gantry, a cooling assembly, and a sliding device. The gantry assembly may include a main gantry and a gantry base configured to support the main gantry. The cooling assembly may be configured to cool the heat generating component. The sliding device may be configured underneath the cooling assembly to facilitate mounting of the cooling assembly.

A further aspect of the present disclosure relates to a system for imaging. The system may include a detector assembly and a gantry assembly. The detector assembly may include a plurality of detector modules and a detector support configured to support the plurality of detector modules, wherein the detector support may have a plurality of guide units, and the plurality of guide units may be configured to facilitate mounting of the plurality of detector modules and limit movement of the plurality of detector modules. The gantry assembly may include a main gantry, a back cover plate, and a gantry base configured to support the main gantry, wherein a portion of the main gantry may form a front face of a scanning channel, a portion of the back cover plate may form a back face of the scanning channel, a portion of the detector assembly may form a sidewall of the scanning channel, and the detector assembly may be mounted on the main gantry and the back cover plate.

A further aspect of the present disclosure relates to a system for PET imaging. The PET system may include a scanning channel with a front face and a back face, a detector assembly including a plurality of detector modules surrounding the scanning channel, a first ring, and a second ring. The first ring may be configured on a first side of the detector assembly facing the front face of the scanning channel. The second ring may be configured on a second side of the detector assembly facing the back face of the scanning channel, wherein at least one of the first ring or the second ring may include at least two segments.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
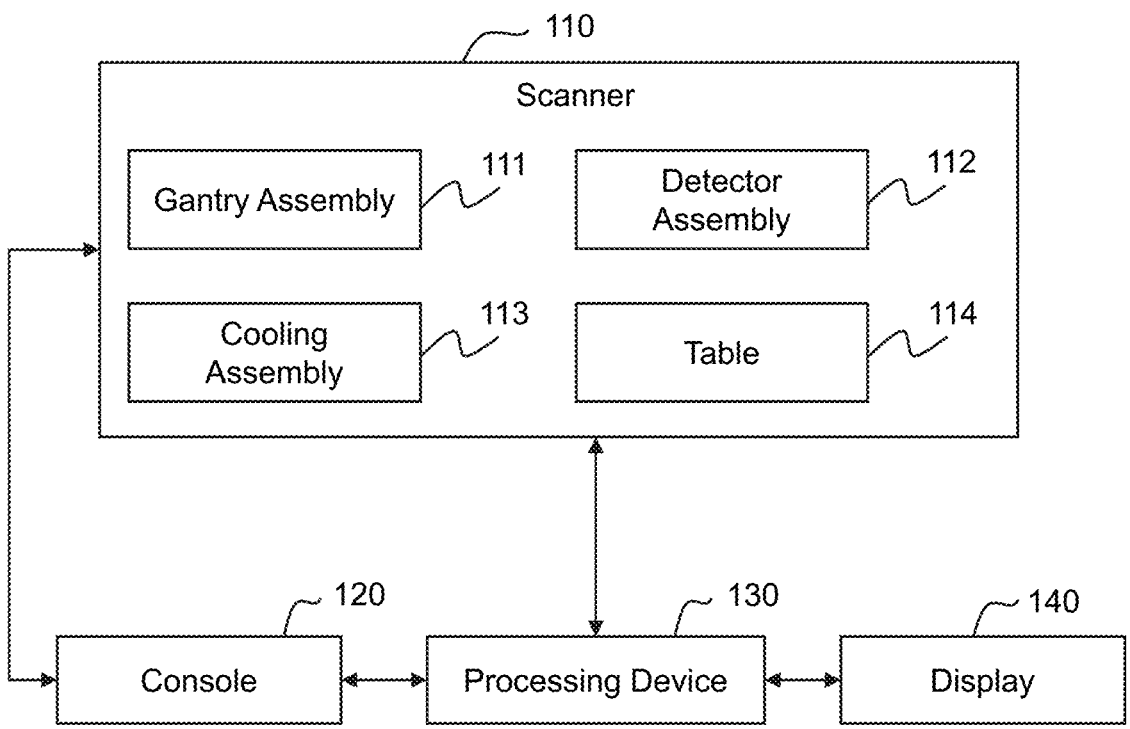
FIG. 1 is a block diagram illustrating an exemplary imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry include been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expression if they may achieve the same purpose.

It will be further understood that the terms "cover," "plate," "base," "piece," "rail," "hole," "ring," "component," "assembly," "layer," etc., when used in this disclosure, refer to one or more parts with one or more specific purposes. However, a structure that may perform a same or similar function compared to a part exemplified above or referred to elsewhere in the present disclosure may be named differently from the present disclosure.

It will be understood that when a unit, engine, module or block is referred to as being "on," "connected to" or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Provided herein are systems and components for non-invasive biomedical imaging, such as for disease diagnostic or research purposes. The system may include a single imaging modality or multiple imaging modalities for conducting different medical scans or studies, including but not limited to ultrasound scan, X-ray scan, bone densitometry, fluoroscopy, computed tomography (CT), digital radiography (DR), single photon emission computed tomography (SPECT), magnetic resonance imaging (MRI), positron emission tomography (PET), or the like, or any combination thereof.

The term "imaging modality" or "modality" as used herein broadly refers to an imaging method or technology that gathers, generates, processes and/or analyzes imaging information of a target body through a particular mechanism. The term "target body" or "object" as used herein broadly relates to any organic or inorganic mass, natural or man-made to be imaged or examined. Exemplary embodiments of a target body pertaining to the present disclosure include cells, tissues, organs or whole bodies of human or animal. Other exemplary embodiments of a target body include but not limited to a man-made composition of organic and/or inorganic matters that are with or without life.

Accordingly, a multi-modality imaging system of the present disclosure can include more than one imaging modality, such as two, three, or more different modalities. In a multi-modality system, the mechanisms through which different imaging modalities operate or function may be the same or different. Accordingly, the imaging information may also be the same or different. For example, in some embodiments, the imaging information may be internal and/or external information, functional and/or structural information of the target body, or the like, or a combination thereof. In some embodiments, the imaging information of different modalities may complement one another, thereby providing a set of imaging data describing a target body. For example, in some embodiments, the multi-modality imaging may achieve the merging of morphological and functional images.

The above types of imaging modalities that may be included in the present system are not exhaustive and are not limiting. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

FIG. 1 is a block diagram illustrating an exemplary imaging system 100 according to some embodiments of the present disclosure. An imaging system 100 may generate an image of an object. The object may include a biological object and/or a non-biological object. The biological object may be a human being, an animal, a plant, or a portion thereof (e.g., a cell, a tissue, an organ, etc.). In some embodiments, the object may be a man-made composition of organic and/or inorganic matters that are with or without life. In the present disclosure, "object" and "subject" are used interchangeably. As illustrated, the imaging system 100 may include a scanner 110, a console 120, a processing device 130, and a display 140.

The scanner 110 may scan an object, and generate a plurality of data relating to the object. In some embodiments, the scanner 110 may be a medical imaging device, for example, a PET device, a SPECT device, a CT device, an MRI device, or the like, or any combination thereof (e.g., a PET-CT device, a PET-MRI device, or a SPECT-MRI device). As illustrated, the scanner 110 may include a gantry assembly 111, a detector assembly 112, a cooling assembly 113, and a table 114. The gantry assembly 111 may be configured to support one or more parts of the scanner 110, for example, the detector assembly 112, the cooling assembly 113, etc. In some embodiments, the gantry assembly 111 may include a scanning channel (or referred to as a detection channel or detection region) where the object is positioned for scanning. More descriptions regarding the gantry assembly 111 may be found elsewhere in the present disclosure. See, e.g., FIG. 2 and the description thereof. The detector assembly 112 may be configured to detect signals, for example, attenuated radioactive rays (e.g., X rays), radiation events (e.g., gamma photons), etc. More descriptions regarding the detector assembly 112 may be found elsewhere in the present disclosure. See, e.g., FIG. 3 and the description thereof. The cooling assembly 113 may be configured to produce, transfer, deliver, channel, or circulate a cooling medium to the scanner 110 to absorb heat produced by the scanner 110 (e.g., the detector assembly 112) during an imaging procedure. More descriptions regarding the cooling assembly 113 may be found elsewhere in the present disclosure. See, e.g., FIG. 4 and the description thereof. The table 114 may be configured to support and/or transport the object (e.g., a patient) to be scanned.

The console 120 may control the scanner 110, the processing device 130, and the display 140. The console 120 may receive signals or instructions from or send information to the scanner 110, the processing device 130, the display 140, and/or other modules or units in the imaging system 100. In some embodiments, the console 120 may include or provide a computer, a program, an algorithm, software, a storage device, one or more interfaces, etc. Exemplary interfaces may include the interfaces of the scanner 110, the processing device 130, the display 140, and/or other modules or units in the imaging system 100. In some embodiments, the console 120 may receive instructions from peripheral units (e.g., an input/output) provided by a user, and send commands to the scanner 110, the processing device 130, and the display 140. In some embodiments, the console 120 may receive commands from the display 140 provided by, e.g., a user, adjust the scanner 110 to detect image data of an object of interest, and control the processing device 130 to process the image data detected by the scanner 110 according to the received commands. In some embodiments, the console 120 may control data storage of the imaging system 100. For instance, the console 120 may control the location of data storage, the contents of data storage, the structure of data storage, the indexing of the stored data, or the like, or a combination thereof.

The processing device 130 may process image data obtained from the scanner 110. For example, the processing device 130 may reconstruct an image based on the image data. In some embodiments, the processing device 130 may be a single server or a server group. The server group may be centralized or distributed. In some embodiments, the processing device 130 may be local or remote from other components in the imaging system 100. The processing device 130 may access image data stored in the scanner 110 via a network. Alternatively, the processing device 130 may be directly connected to the scanner 110 to access stored image data. In some embodiments, the processing device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 130 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

The display 140 may receive input and/or display output information. The input and/or output information may include programs, software, algorithms, data, text, number, images, voice, or the like, or any combination thereof. For example, a user or an operator may input one or more initial parameters or conditions to initiate a scan. As another example, some information may be imported from an external resource, such as a floppy disk, a hard disk, a wireless terminal, or the like, or any combination thereof. As still another example, the display 140 may display one or more images processed by the processing device 130.

It should be noted that the above description is merely provided for the purposes of illustration, and not intended to limit the scope of the present disclosure. For persons having ordinary skills in the art, multiple variations and modifications may be made under the teachings of the present disclosure. For example, the imaging system 100 may include one or more storage devices. However, those variations and modifications do not depart from the scope of the present disclosure.

Figure 2:
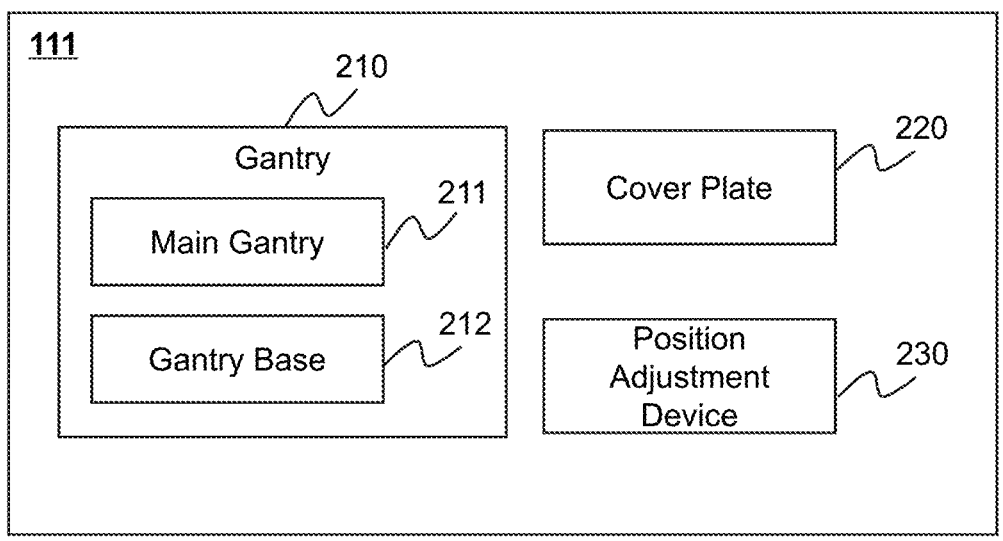
FIG. 2 is a block diagram illustrating an exemplary gantry assembly according to some embodiments of the present disclosure.

FIG. 2 is a block diagram illustrating an exemplary gantry assembly 111 according to some embodiments of the present disclosure. The gantry assembly 111 may include a gantry 210, a cover plate 220, and a position adjustment device 230.

The gantry 210 may be configured to support one or more parts of the scanner 110, for example, the detector assembly 112, the cooling assembly 113, etc. As illustrated, the gantry 210 may include a main gantry 211 and a gantry base 212. In the present disclosure, "main gantry" and "main mounting plate" may be used interchangeably. The main gantry 211 may provide a main frame structure for the scanner 110. The main gantry 211 may include a scanning channel. The gantry base 212 may be configured to support the cooling assembly 113, the detector assembly 112, the main gantry 211, and/or the cover plate 220. For example, the gantry base 212 may include a guide component corresponding to a sliding device of the cooling assembly 113. The main gantry 211 may be connected with the gantry base 212. More descriptions regarding the gantry base 212 may be found elsewhere in the present disclosure. See, e.g., FIGS. 19 and 20 and the description thereof.

The cover plate 220 may be configured to cover the gantry 210. In some embodiments, the cover plate 220 may include one or more cover plates, for example, a front cover plate, a back cover plate, a side cover plate (e.g., a circular cover plate), etc. The front cover plate may be configured to cover the front side of the gantry 210. The back cover plate may be configured to cover the back side of the gantry 210. The side cover plate may be configured to cover the detector modules 310.

The position adjustment device 230 may be configured to adjust a position of a component. In some embodiments, the position adjustment device 230 may adjust the position of a first component relative to the position of a second component. For example, the position adjustment device 230 may adjust the position of the main gantry 211 relative to the position of the front cover plate. More descriptions regarding the position adjustment device 230 may be found elsewhere in the present disclosure. See, e.g., FIG. 9 through FIG. 11 and the description thereof.

It should be noted that the above description of the diagram in FIG. 2 is merely provided for the purposes of illustration, and not intended to limit the scope of the present disclosure. For persons having ordinary skills in the art, multiple variations or modifications may be made under the teachings of the present disclosure. For example, the gantry assembly 111 may further include one or more components, such as one or more connecting pieces to connect the main gantry 211 and the gantry base 212. As another example, the position adjustment device 230 may be unnecessary and may be omitted.

Figure 3:
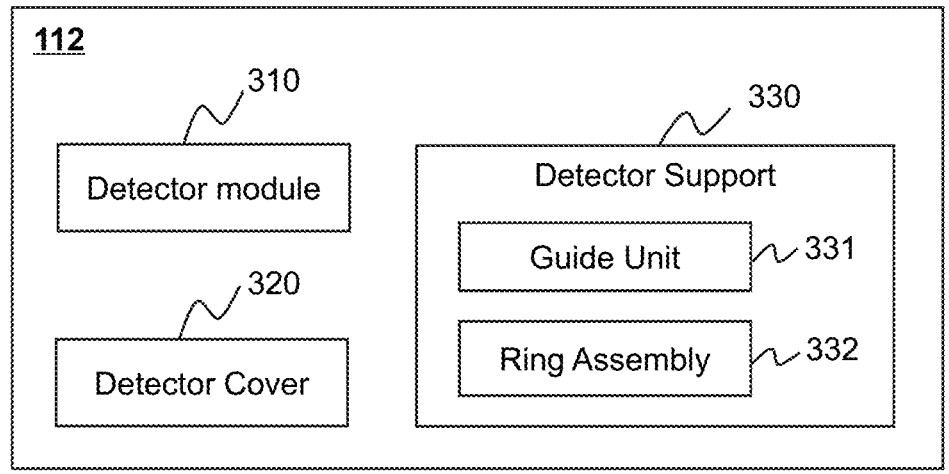
FIG. 3 is a block diagram illustrating an exemplary detector assembly according to some embodiments of the present disclosure.

FIG. 3 is a block diagram illustrating an exemplary detector assembly 112 according to some embodiments of the present disclosure. The detector assembly 112 may include a detector module 310, a detector cover 320, and a detector support 330.

The detector module 310 may be configured to detect signals, for example, attenuated radioactive rays, radiation events, etc. Merely by way of example, for a PET system, the detector module 310 may detect gamma photons. The detector module 310 of a PET system may include an electronics unit and a detector unit. The detector unit may receive radiation rays (e.g., gamma rays) and generate electrical signals. The electronics unit may collect and/or process the electrical signals generated by the detector unit.

The detector cover 320 may be configured to cover the detector module 310 and/or the detector support 330 circumferentially. The detector cover 320 may protect the detector support 330 and/or the detector module 310 from dust and dirt. In some embodiments, the detector cover 320 and the cover plate 220 may form a space for the detector module 310. In some embodiments the detector cover 320 may form a space for cooling the detector module 310. The detector cover 320 may be configured as a side cover plate of the gantry assembly 111. In some embodiments, the detector cover 320 may be a circular shell or housing. In some embodiments, the detector cover 320 may include one or more sub detector covers. More descriptions regarding the detector cover 320 may be found elsewhere in the present disclosure. See, e.g., FIG. 12.

The detector support 330 may be configured to support the detector module 310. In some embodiments, the detector support 330 may be attached to the main gantry 211. The detector support 330 may be covered by a front cover plate, a back cover plate, and a side cover plate (e.g., the detector cover 320). The detector support 330 may be configured such that it surrounds the scanning channel. As illustrated, the detector support 330 may include one or more guide units 331 and a ring assembly 332. The guide unit 331 may guide the positioning of the detector module 310 for assembly or in operation. In some embodiments, the guide unit 331 may include one or more guide plates. The guide plates may be configured along an axial direction of the scanning channel. More descriptions regarding the guide unit 331 may be found elsewhere in the present disclosure. See, e.g., FIGS. 17 and 18 and the description thereof. The ring assembly 332 may include a ring made of lead or any other suitable material. For example, the ring assembly 332 may be made of bismuth (Bi), platinum (Pt), lead, etc. The ring assembly 332 may be configured to prevent the detector module 310 from detecting radiation rays (e.g., gamma photons) emitted from outside of a region of interest of an object that is located outside of an imaging area of the PET imaging device. In some embodiments, the ring assembly 332 may include one or more segments. More descriptions regarding the ring assembly 332 may be found elsewhere in the present disclosure. See, e.g., FIG. 15 and the description thereof.

It should be noted that the above description of the diagram in FIG. 3 is merely provided for the purposes of illustration, and not intended to limit the scope of the present disclosure. For persons having ordinary skills in the art, multiple variations or modifications may be made under the teachings of the present disclosure. For example, the detector assembly 112 may further include one or more components, such as one or more connecting pieces to connect the detector module 310 and the detector support 330. As another example, the detector cover 320 and/or the ring assembly 332 may not be necessary and may be omitted.

Figure 4:
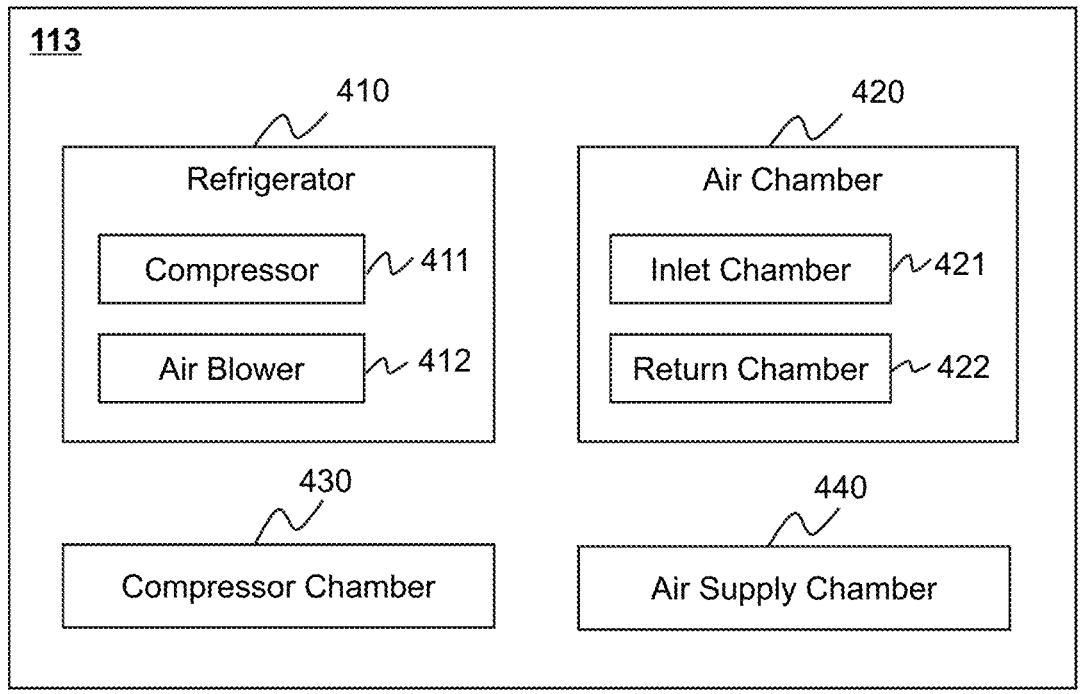
FIG. 4 is a block diagram illustrating an exemplary cooling assembly according to some embodiments of the present disclosure.

FIG. 4 is a block diagram illustrating an exemplary cooling assembly 113 according to some embodiments of the present disclosure. The cooling assembly 113 may include a refrigerator 410, an air chamber 420, a compressor chamber 430, and an air supply chamber 440. More descriptions regarding the cooling assembly 113 may be found elsewhere in the present disclosure. See, e.g., FIGS. 22 and 23.

The refrigerator 410 may process (or cool down) and drive a cooling medium. The cooling medium may include a cooling gas (e.g., air), or a cooling liquid (e.g., water). The cooling medium may absorb heat from the scanner 110.

As exemplified in FIG. 4, the refrigerator 410 may include a compressor 411 and an air blower 412 when the cooling medium is a gas (e.g., air). In some embodiments, the compressor 411 may use a cryogen and/or a refrigerant to cool the cooling medium. The compressor 411 (also referred to as a heat exchanger) may increase the pressure of the cryogen, and then, the cryogen may be condensed, and the heat in the cryogen may dissipate to a heat sink (not shown). In some embodiments, condensed cryogen may evaporate in an evaporator (not shown), and absorb heat from the cooling medium, and then the cooling medium may be cooled down. In some embodiments, the compressor 411 may include a shell and tube heat exchanger, a pillow plate heat exchanger, a fluid heat exchanger, a dynamic scraped surface heat exchanger, a phase-change heat exchanger, a direct contact heat exchanger, or the like, or any combination thereof. The air blower 412 (e.g., a fan) may drive the cooling medium into one or more cooling medium passages. The cooling medium passages may channel the cooling medium to one or more target locations (e.g., around the detector module 310) of the scanner 110. In some embodiments, the air blower 412 may regulate the flow rate of the cooling medium. The flow rate of the cooling medium may be regulated through the variation of the rotation speed of the air blower 412.

The air chamber 420 may be configured as part of the cooling medium passages. As illustrated, the air chamber 420 may include an inlet chamber 421 and a return chamber 422. The inlet chamber 421 may connect the air blower 412 and a chilling chamber. The chilling chamber may be configured with one or more heating components (e.g., the detector module 310) of the scanner 110. The return chamber 422 may connect the chilling chamber and the compressor 411. The compressor chamber 430 may be configured with the compressor 411. The air supply chamber 440 may be configured to feed air to the air blower 412.

FIG. 4 illustrates an exemplary configuration of a cooling assembly that uses air (or another type of gas or a mixture of different types of gases as the cooling medium. A cooling assembly that uses a liquid cooling medium may be configured similarly. It should be noted that the above description of the diagram in FIG. 4 is merely provided for the purposes of illustration, and not intended to limit the scope of the present disclosure. For persons having ordinary skills in the art, multiple variations or modifications may be made under the teachings of the present disclosure. For example, the cooling assembly 113 may further include one or more components, such as one or more thermal insulation layers. The thermal insulation layers may prevent or reduce heat exchange between the cooling medium in different chambers that share a common surface.

Figure 5A:
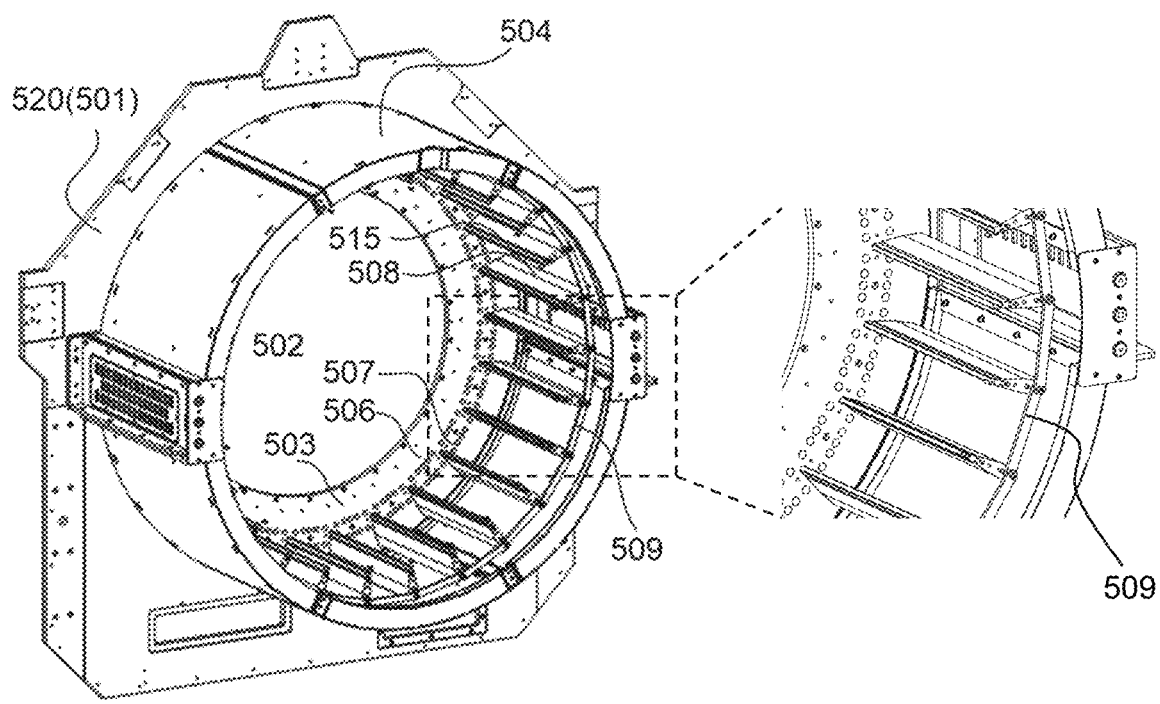
FIGS. 5A and 5B illustrate structural components of an exemplary scanner according to some embodiments of the present disclosure.
Figure 5B:
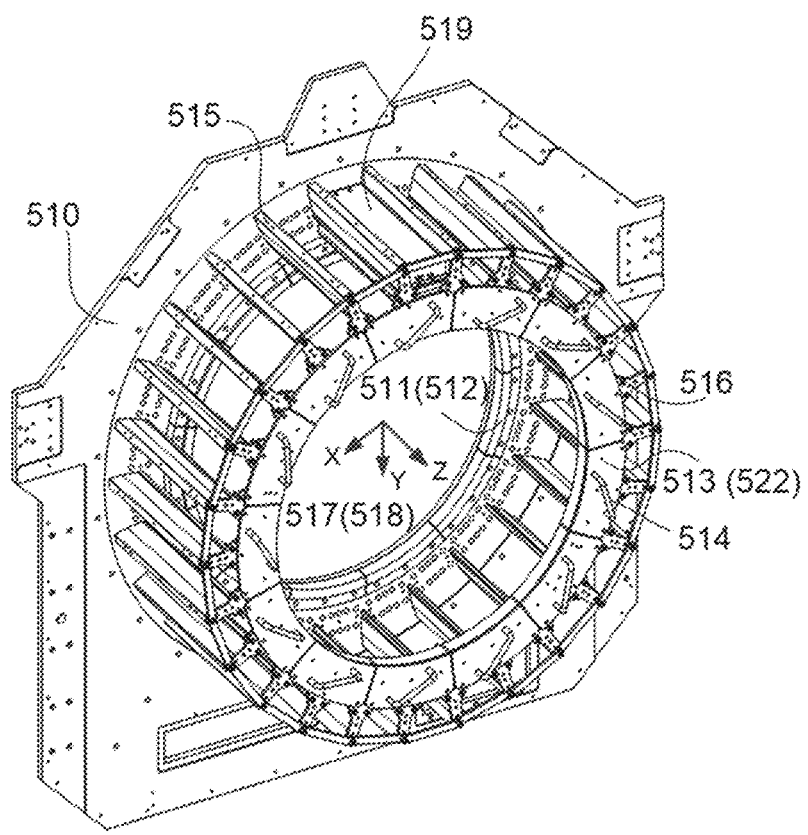

FIGS. 5A and 5B illustrate structural components of an exemplary scanner 110 according to some embodiments of the present disclosure. As illustrated in FIG. 5A, the scanner 110 may include a main gantry 501 (also referred to as a shared plate 520), a scanning channel 502, a chilling chamber 503, a detector cover 504, a limit plate 515, an air intake 506, an air outlet 507, a guide unit 508, and a limit piece 509. The main gantry 501 may be the same as or similar to the main gantry 211. The scanning channel 502 may define an imaging area where the object may be positioned to be scanned or imaged. The chilling chamber 503 may be configured to cool the heat generating components of the scanner 110. In some embodiments, the chilling chamber 503 may be divided into a plurality of sub chambers. The detector cover 504 may be the same as or similar to the detector cover 320. The limit plate 515 may divide the chilling chamber 503 into two or more sub chambers. The chilling chamber 503 may include the air intake 506 and the air outlet 507. In some embodiments, the air intake 506 and the air outlet 507 may be configured on each sub chamber of the chilling chamber 503. In some embodiments, a sub chamber may contain a detector unit.

Figure 18A:
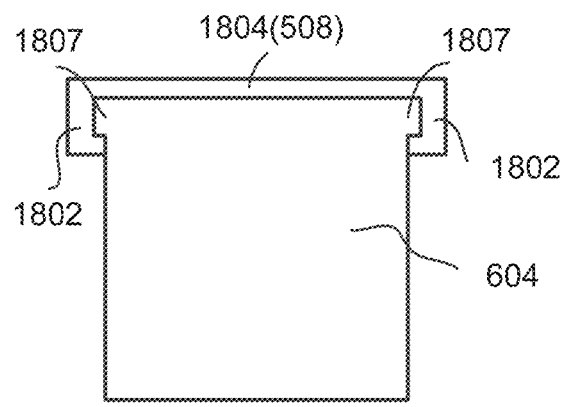
FIG. 18A illustrates an exemplary detector module and an exemplary guide unit according to some embodiments of the present disclosure.
Figure 18B:
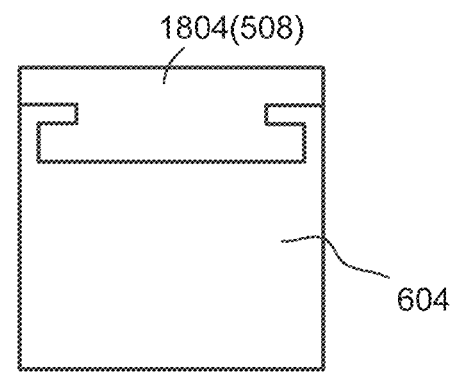
FIG. 18B illustrates an exemplary detector module and an exemplary guide unit according to some embodiments of the present disclosure.
Figure 18C:
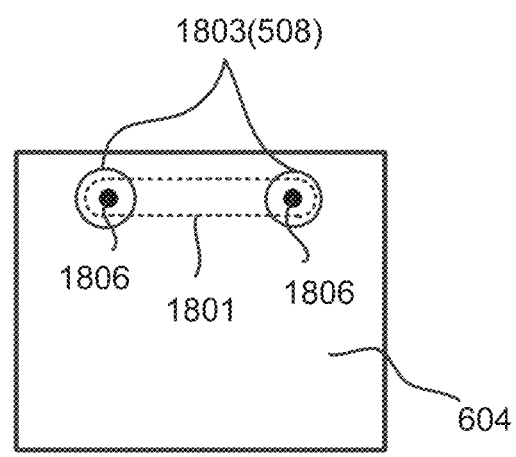
FIG. 18C illustrates an exemplary detector module and an exemplary guide unit according to some embodiments of the present disclosure.

The guide unit 508 may be configured on a detector support around the scanning channel 502 to guide the positioning of the detectors for assembly or in operation. In some embodiments, the guide unit 508 may be a guide plate as illustrated in FIGS. 18A and 18B. In some embodiments, the guide unit 508 may be a guide column as illustrated in FIG. 18C. The limit piece 509 may be configured on the guide unit 508 to limit the detector modules from sliding off the guide unit 508. In some embodiments, the limit piece 509 may be located at one end of the guide unit 508 away from the main gantry 501. The limit piece 509 may restrict the position of the detector modules relative to the guide unit 508. In some embodiments, in the assembly of a scanner, the detector modules may slide along the guide unit 508 and then be fixed in position by the limit piece 509. In some embodiments, the detector modules may be fixed in position using the limit piece 509, without using one or more screws on the detector modules themselves. Thus, the assembly and disassembly of the detector modules may be simplified. The limit piece 509 may be a thin stripe mounted using, e.g., one or more screws, on one end of the limit plate 515 that is away from the main gantry 501. In some embodiments, the guide unit 508 may be arranged perpendicular to a front side of the main gantry 501. Thus, a technician may stand at one side opposite to the front side of the main gantry 501 and handle (e.g., assemble, maintain, dissemble) the detector modules. In some embodiments, the guide unit 508 may include a guide plate arranged along an axial direction of the scanning channel 502, the guide plate may include a guide rail, and the detector module(s) may include at least one guide piece complementary to the guide rail.

In some embodiments, the limit piece 509 may include one or more sub limit pieces. One or more sub limit pieces may be used with a detector module. In some embodiments, a detector module may be limited by one sub limit piece. In some embodiments, each detector module may have a corresponding limit piece (or sub limit piece). Thus, a technician may dissemble and/or maintain the detector module by removing the sub limit piece, without dissembling the whole limit piece 509. The maintenance of the detector modules may be simplified in this way. In some embodiments, the limit piece 509 may be configured as an integral part to limit a plurality of detector modules. As shown in an enlarged view of the limit piece 509 in FIG. 5A, the limit piece 509 may have a curved shape (e.g., the shape of a ring, an arc, etc.). When assembling the detector modules, a technician may slide the detector modules along the guide unit 508, and then the detector modules may be limited by the limit piece 509. It should be noted that the limit piece 509 described in the present disclosure is merely an exemplary mechanism for fixing the positions of a plurality of detector modules. The positions of the plurality of detector modules may be fixed in other ways, for example, by way of engagement.

As illustrated in FIG. 5B, the scanner 110 may include a gantry 510, a first ring 511 (including one or more first segments 512), a second ring 513 (including one or more second segments 522), one or more handles 514, one or more limit plates 515 (also referred to as guide plates in some embodiments), a detector cover 516, a scanning channel space 517 (also referred to as a scanning channel 518), and one or more detector modules 519 (also referred to as the detector assembly 112). The gantry 510 may be the same as or similar to the main gantry 501. In some embodiments, the first ring 511 or the second ring 513 may be unnecessary. The limit plates 515 may be fixed on the gantry 510 along the axial direction of the scanning channel 518 (i.e., the Z axis) via one or more screws. In some embodiments, the orientation of the limit plates 515 may be perpendicular to a front side of the gantry 510. A detector module 519 may be the same as or similar to the detector module 310 including one or more electronics units and one or more detector units. In the present disclosure, the X axis direction shown in FIG. 5B may be from the right side to the left side of the gantry 510. The Y axis direction shown in FIG. 5B may be from the upper part to the lower part of the gantry 510. The Z axis direction shown in FIG. 5B may be from the front side to the rear side of the gantry 510 along the axis of the scanning channel 518. In some embodiments, the detector assembly 112 may have a first side and a second side along an axial direction of the scanning channel 502. The first side may be closer to the front face of the scanning channel 502. In some embodiments, the detector assembly 112 may include a first ring 511 located on the first side of the detector assembly 112 and a second ring 513 located on the second side of the detector assembly 112. In some embodiments, at least one of the first ring 511 or the second ring 513 may include at least two segments. In some embodiments, the first ring 511 and/or the second ring 513 may include a flange including a protrusion toward the detector modules 519.

The first segments 512 may be fixed on an edge of the scanning channel 518, forming the first ring 511. The first ring 511 may be closer to the front side of the gantry 510 than the limit plates 515. Before the detector modules 519 are assembled, the first ring 511 and the limit plates 515 may be fixed on the gantry 510. Then one of the detector modules 519 may be fixed between two adjacent limit plates 515 by sliding on one or more guiding rails (not shown in FIG. 5B). The guiding rail(s) may be mounted or formed (e.g., carved) on the limit plates 515 and arranged along the axial direction of the scanning channel 518 (i.e., the Z axis). The immobilization of a detector module 519 and the limit plates 515 in the radial direction of the scanning channel 518 may be realized through the guiding rail(s). Further, the second segments 522 may be fixed on an end of the limit plates 515 that is away from the gantry 510, forming the second ring 513. The first ring 511 and the second ring 513 may be configured to block undesired gamma photons from entering the scanning channel 518. The second ring 513 may restrict the position of the detector modules 519 relative to the limit plates 515 along the axial direction of the scanning channel 518. The number of the second segments 522 may relate to the number of the limit plates 515. The number of the limit plates 515 may relate to the number of the detector modules 519. Accordingly, the number of the second segments 522 may relate to the number of the detector modules 519. In some embodiments, the number of the detector modules 519 is an integral multiple of the number of the second segments 522. The integral multiple may be 2, 3, 4, 5, etc. Merely by way of example, if the number of the detector modules 519 is 26, the number of the second segments 522 may be half of that of the detector modules 519, i.e., 13. In some embodiments, a technician may dissemble and/or maintain a specific detector module 519 by removing a corresponding second segment 522 that limits the specific detector module 519, without dissembling the whole second ring 513. The maintenance of the detector modules may be simplified in this way. In some embodiments, a handle 514 may be mounted on a side of a second segment 522 away from a detector module 519. The handles 514 may be of a U shape, a T shape, an L shape, etc. The handles 514 may facilitate the handling (e.g., assembly, maintenance, disassembly) of the second segments 522. More descriptions regarding the first ring 511 and/or the second ring 513 may be found elsewhere in the present disclosure. See, e.g., FIGS. 15 and 16 and the description thereof.

Figure 6A:
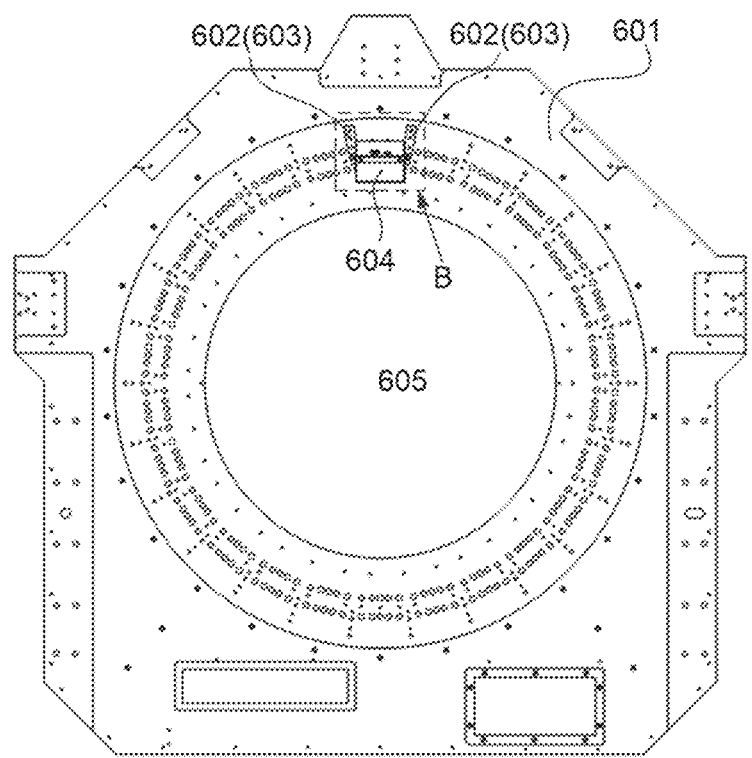
FIG. 6A illustrates a front view of an exemplary scanner according to some embodiments of the present disclosure.

FIG. 6A illustrates a front view of an exemplary scanner 110 according to some embodiments of the present disclosure. As illustrated in FIG. 6A, the scanner 110 may include a main gantry 601 (also referred to as a main mounting plate), one or more guide plates 602, one or more detector modules 604, and a scanning channel 605. In some embodiments, the main gantry 601 and the main gantry 501 (or the gantry 510) may be the same or different. The guide plates 602 may correspond to the limit plates 515 as discussed in connection with FIG. 5. In some embodiments, the limit plate(s) 515 may take a form different from the guide plate(s) 602. For instance, the limit plate(s) 515 may take the form of one or more guide pieces 603. The region B shown in FIG. 6A may illustrate one detector module 604 and two corresponding guide plates 602. More descriptions regarding the region B may be found elsewhere in the present disclosure. See, e.g., FIG. 17A and the description thereof.

Figure 6B:
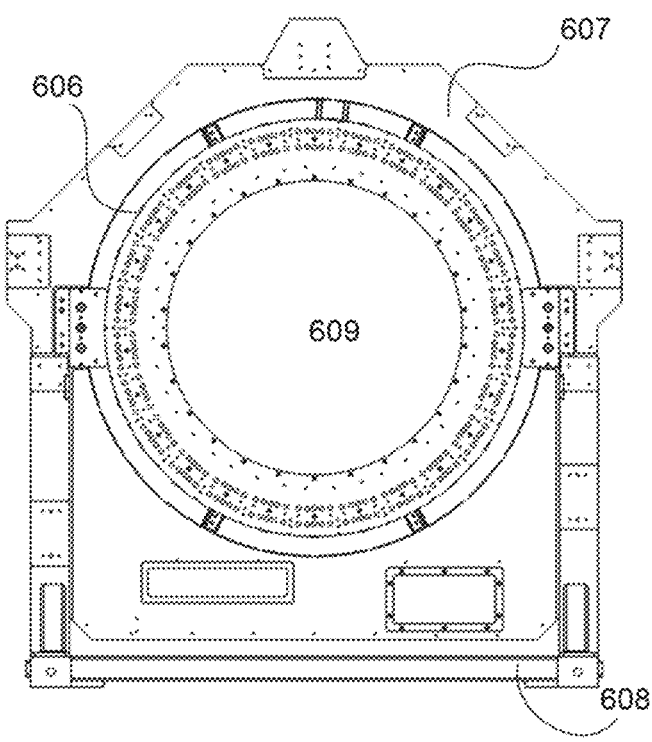
FIG. 6B illustrates a front view of an exemplary scanner according to some embodiments of the present disclosure.

FIG. 6B illustrates a front view of an exemplary scanner 110 according to some embodiments of the present disclosure. As illustrated in FIG. 6B, the scanner 110 may include a detector cover 606, a front cover plate 607, a gantry base 608, and a scanning channel 609. The front cover plate 607 may be substantially vertical. In some embodiments, the front cover plate 607 and the main gantry 601 may be the same or different. In some embodiments, the scanning channel 609 and the scanning channel 605 may be the same or different. The gantry base 608 may be located on the bottom of the scanner 110.

Figure 6C:
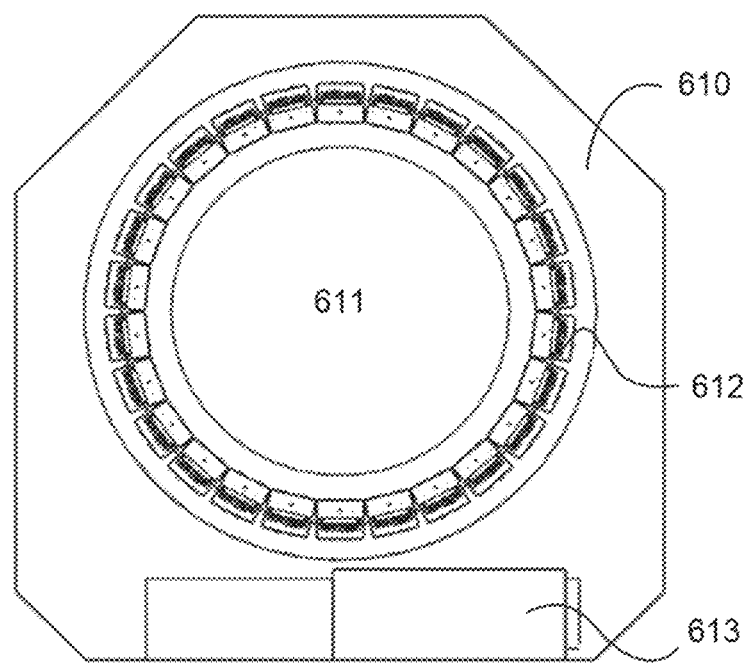
FIG. 6C is a schematic diagram illustrating an exemplary scanner according to some embodiments of the present disclosure.

FIG. 6C is a schematic diagram illustrating an exemplary scanner 110 according to some embodiments of the present disclosure. As illustrated in FIG. 6C, the scanner 110 may include a gantry 610, a scanning channel 611, one or more detector modules 612, and a cooler 613. In some embodiments, the gantry 610 and the main gantry 601 may be the same or different. In some embodiments, the scanning channel 611 and the scanning channel 605 may be the same or different. The cooler 613 may be the same as or similar to the cooling assembly 113.

Figure 6D:
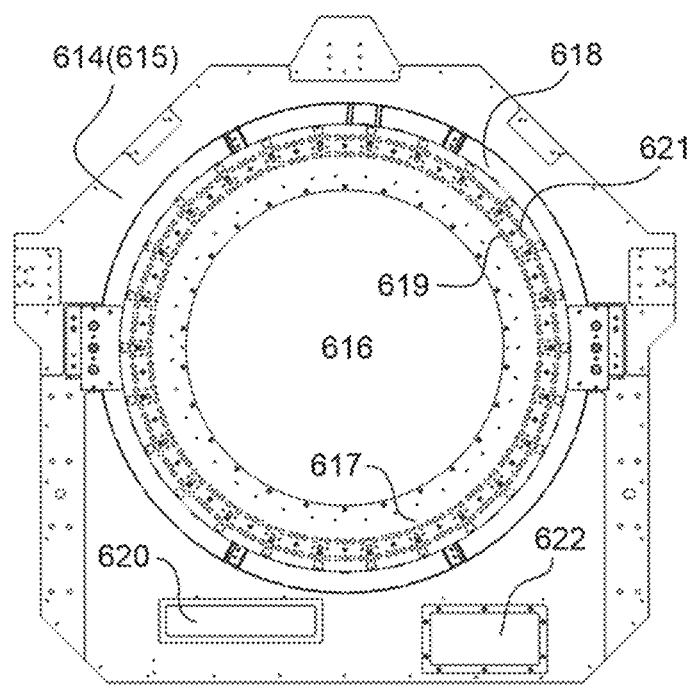
FIG. 6D is a schematic diagram illustrating an exemplary scanner according to some embodiments of the present disclosure.

FIG. 6D is a schematic diagram illustrating an exemplary scanner 110 according to some embodiments of the present disclosure. As illustrated in FIG. 6D, the scanner 110 may include a shared plate 614 (also referred to as a gantry 615), a scanning channel 616, one or more chilling chambers 617, a detector cover 618, one or more air intakes 619 for an inlet chamber, an inlet chamber port 620, one or more air outlets 621 for a return chamber, and a return chamber port 622. The air intakes 619 may be configured on the chilling chamber 617. The air outlets 621 may be configured on the chilling chamber 617. The air intakes 619 may be connected to the air outlets 621 to form a passage for air. In some embodiments, an inlet chamber, a return chamber, the inlet chamber port 620, and/or the return chamber port 622 may be configured on the shared plate 614. In some embodiments, the shared plate 614 and the main gantry 601 may be the same or different. In some embodiments, the shared plate 614 and the shared plate 520 may be the same or different. In some embodiments, the scanning channel 616 and the scanning channel 605 may be the same or different. In some embodiments, the detector cover 618 and the detector cover 504 may be the same or different. In some embodiments, the chilling chamber 617 and the chilling chamber 503 may be the same or different. In some embodiments, the air intakes 619 and the air intake 506 may be the same or different. In some embodiments, the air outlets 621 and the air outlets 507 may be the same or different.

Figure 7A:
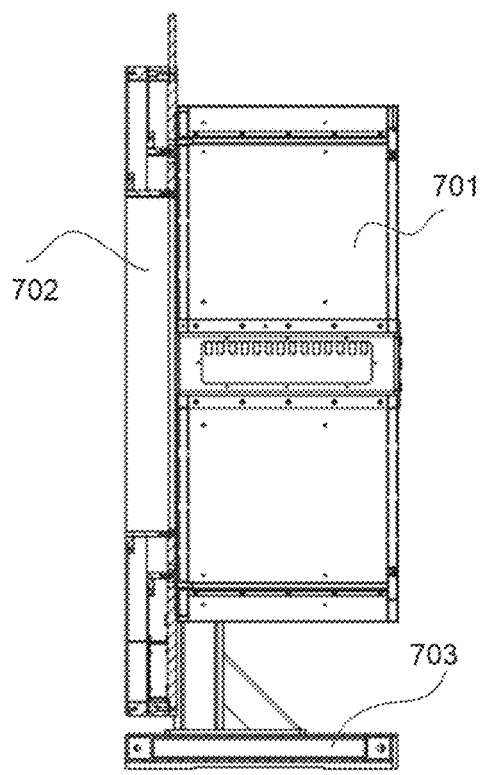
FIGS. 7A and 7B illustrate side views of exemplary scanners according to some embodiments of the present disclosure.
Figure 7B:
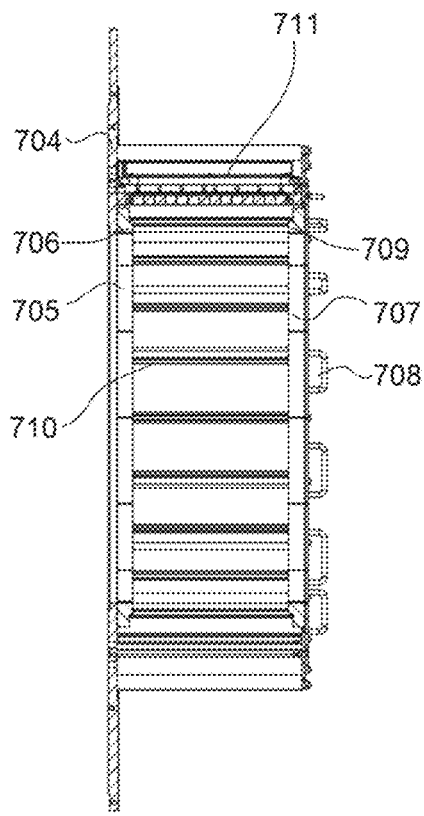

FIGS. 7A and 7B illustrate side views of exemplary scanners 110 according to some embodiments of the present disclosure. As illustrated in FIG. 7A, a scanner 110 may include a detector cover 701, a front cover plate 702, and a gantry base 703. In some embodiments, the front cover plate 702 and the front cover plate 607 may be the same or different. In some embodiments, the detector cover 701 and the detector cover 606 may be the same or different. In some embodiments, the gantry base 703 and the gantry base 608 may be the same or different. As illustrated in FIG. 7B, a scanner 110 may include a gantry 704, a first ring 705, a first flange 706, a second ring 707, a handle 708, a second flange 709, one or more limit plates 710, and one or more detector modules 711. The first flange 706 may be formed on the first ring 705. The second flange 709 may be formed on the second ring 707. The first flange 706 and the second flange 709 may bulge toward the detector modules 711. The first flange 706 and the second flange 709 may block undesirable radiation rays (e.g., gamma photons) emitted by an object positioned outside an imaging region. In some embodiments, a front face of the detector cover 701 may include at least one first flange (e.g., the first flange 706). The first flange may include a protrusion toward an axial direction of the detector cover 701. In some embodiments, a back face of the detector cover 702 may include at least one second flange (e.g., the second flange 709). The second flange may include a protrusion toward an axial direction of the detector cover 701. In some embodiments, the detector cover 701 may be connected to the front cover plate 702 by the first flange 706 and be connected to a back cover plate (not shown) by the second flange 709. In some embodiments, the front cover plate 702, the detector cover 701, the back cover plate, and a sidewall of a scanning channel (not shown) may surround a detector support of the detector modules 711. In some embodiments, the gantry 704 and the gantry 510 may be the same or different. In some embodiments, the gantry 704 and the front cover plate 702 may be the same or different. In some embodiments, the detector modules 711 and the detector modules 519 may be the same or different. In some embodiments, the first ring 705 and the first ring 511 may be the same or different. In some embodiments, the second ring 707 and the second ring 513 may be the same or different. In some embodiments, the limit plates 710 and the limit plates 515 may be the same or different. In some embodiments, the handle 708 and the handle 514 may be the same or different.

Figure 8A:
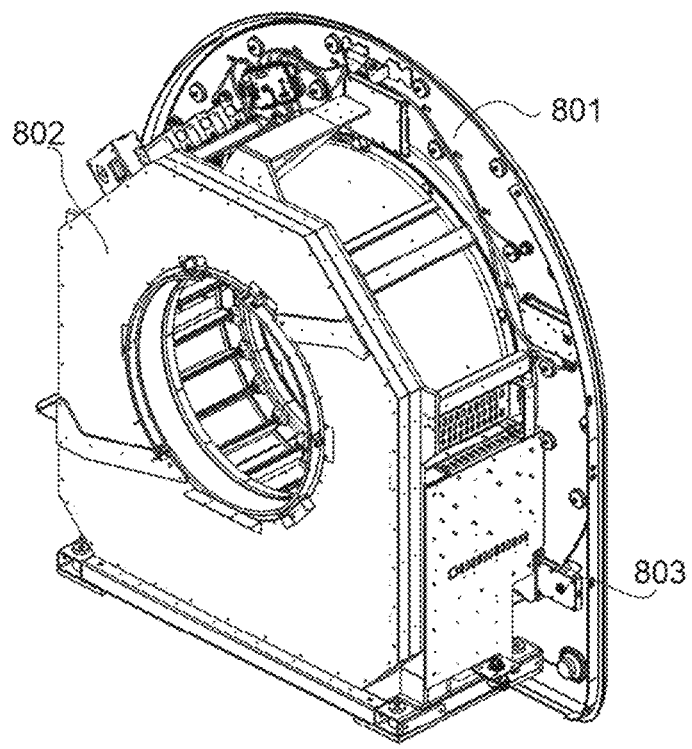
FIGS. 8A through 8C illustrate three views of an exemplary scanner including a position adjustment device according to some embodiments of the present disclosure.
Figure 8B:
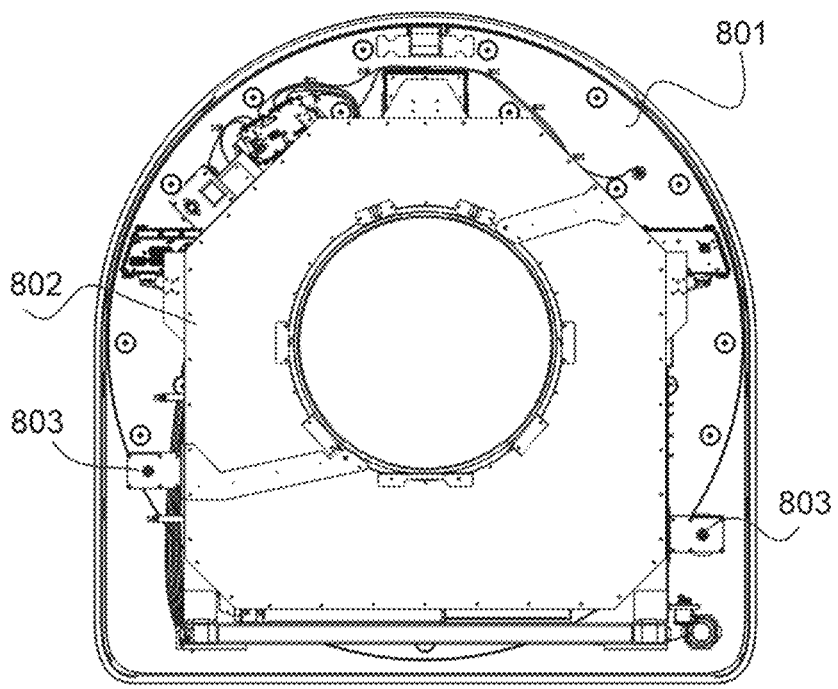
Figure 8C:
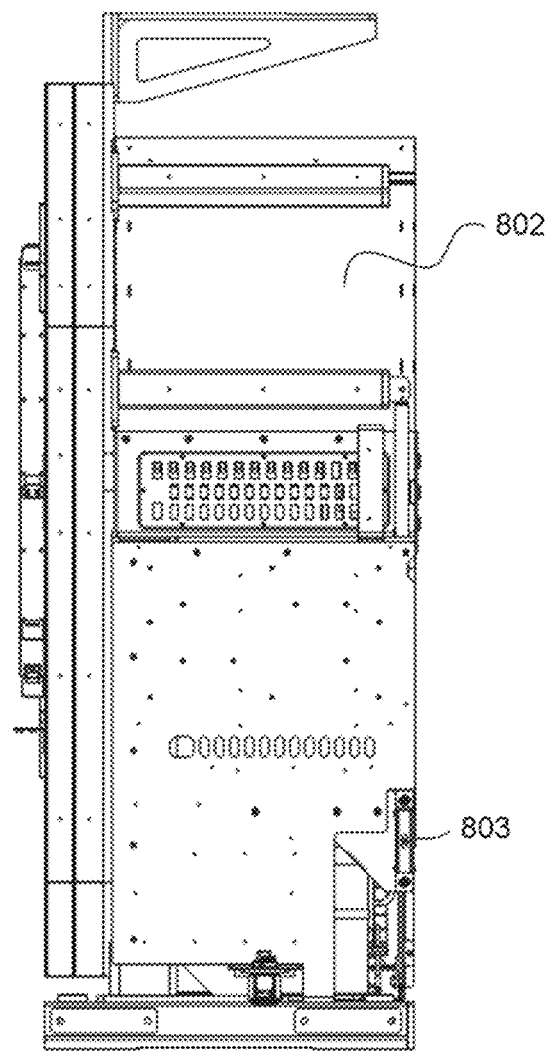

FIGS. 8A through 8C illustrate three views of an exemplary scanner 110 including a position adjustment device according to some embodiments of the present disclosure. As illustrated in FIGS. 8A to 8C, the scanner 110 may include a front cover plate 801, a gantry 802, and a position adjustment device 803. In some embodiments, the front cover plate 801 and the front cover plate 702 may be the same or different. The position adjustment device 803 may be configured to connect a first component (e.g., the front cover plate 801) and a second component (e.g., the gantry 802), and adjust a relative position between the first component and the second component. In some embodiments, the first component and the second component may be connected via at least one (or two, three, etc.) position adjustment device 803. Merely by way of example, the first component and the second component may be connected via two position adjustment devices 803. As illustrated in FIG. 8B, the two position adjustment devices 803 may be located on two different sides of the second component (e.g., the gantry 802) and attached to the first component (e.g., the front cover plate 801). The position adjustment device 803 may include one or more bulged ends, one or more sliding holes configured on the bulged ends, a fixed pin, a fixed hole, etc., as exemplified in FIGS. 9A-9D. The fixed pin may include a fixed plane, a pin, etc., as exemplified in FIG. 10. The position adjustment device 803 may be connected to the gantry 802 via the bulged ends and the sliding holes. The fixed pin may be used to attach, by inserting into the fixed hole, the position adjustment device 803 to a side of the front cover plate 801 that is close to the gantry 802.

Figure 9A:
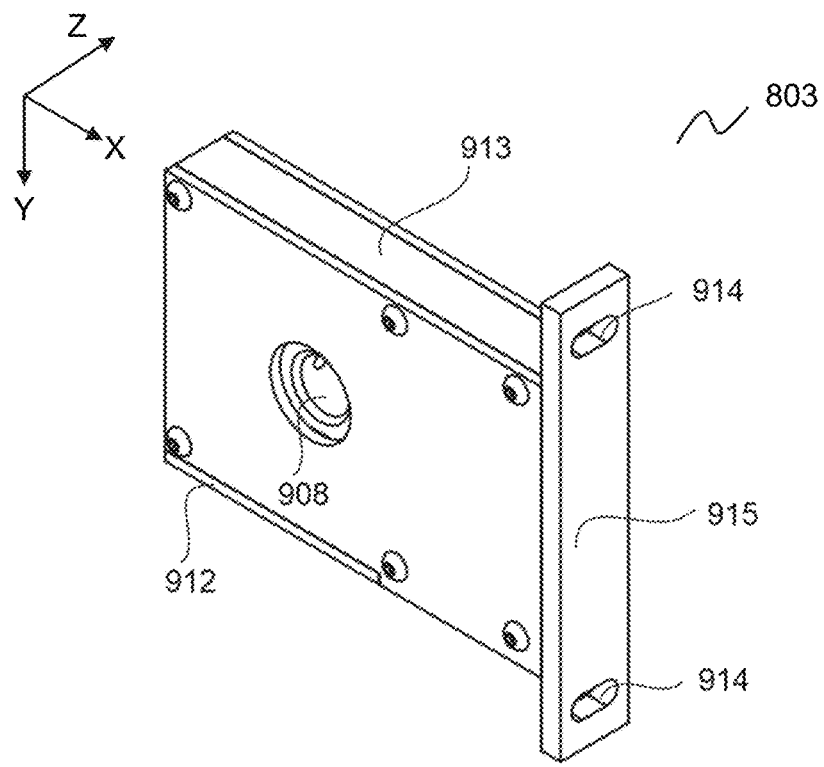
FIG. 9A illustrates an exemplary position adjustment device according to some embodiments of the present disclosure.

FIG. 9A illustrates an exemplary position adjustment device 803 according to some embodiments of the present disclosure. As illustrated, the position adjustment device 803 may include a fixed hole 908, a second fastener 912, a housing 913, and one or more sliding holes 914. In some embodiments, the position adjustment device 803 may further include one or more protruding ends 915. The fixed hole 908 may accommodate a pin (e.g., a pin 1002 of a fixed pin 1000 shown in FIG. 10). The pin 1002 may pass through the fixed hole 908 and fix via a screw. The second fastener 912 may be configured to fix an adjustment piece (e.g., a second adjustment piece 911 shown in FIG. 9C). The second fastener 912 may be configured on the housing 913 via a screw (e.g., a screw 903 shown in FIG. 9D). The sliding holes 914 may be configured to facilitate the attachment of the position adjustment device 803 onto a component (e.g., the front cover plate 801). The sliding holes 914 may be located on the protruding end 915.

Figure 9B:
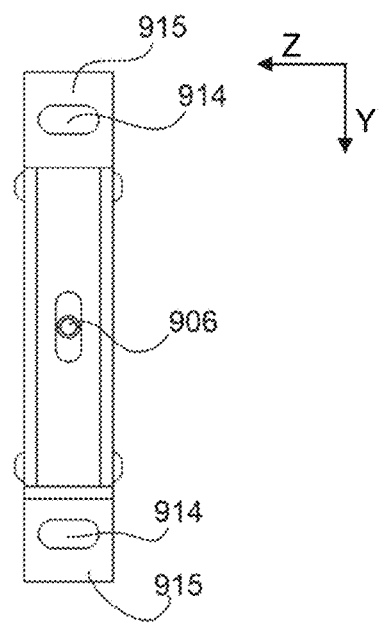
FIG. 9B illustrates a side view of an exemplary position adjustment device according to some embodiments of the present disclosure.

FIG. 9B illustrates a side view of an exemplary position adjustment device 803 according to some embodiments of the present disclosure. The side view may be in a Y-Z plane shown in FIG. 9A. As illustrated in FIG. 9B, the position adjustment device 803 may include a first adjustment piece 906, one or more sliding holes 914, and one or more protruding ends 915. A protruding end 915 may be located on one side of the housing 913 (see FIGS. 9A, 9C, and 9D). The housing 913 may be movable along the Z axis direction. As illustrated in FIGS. 9A and 9D, the protruding end 915 may be longer than the housing 913 along the Y axis direction. The protruding end 915 may be configured with a sliding hole 914. The sliding hole 914 may be configured to facilitate the attachment of the position adjustment device 803 onto a component whose position may be adjusted by the position adjustment device 803. One or more screws may pass through the sliding holes 914 and then attach the position adjustment device 803 onto the component. In some embodiments, the sliding hole 914 may be of a stripe shape, a rectangular shape, a circle shape, etc. Merely by way of example, for the sliding hole 914 having a stripe shape (e.g., the long axis of the stripe is along the Z axis direction), the housing 913 may be moved along the Z axis by moving the screws along the long axis of the sliding hole 914. In some embodiments, the screws may need to be loosened before moving the housing 913.

Figure 9C:
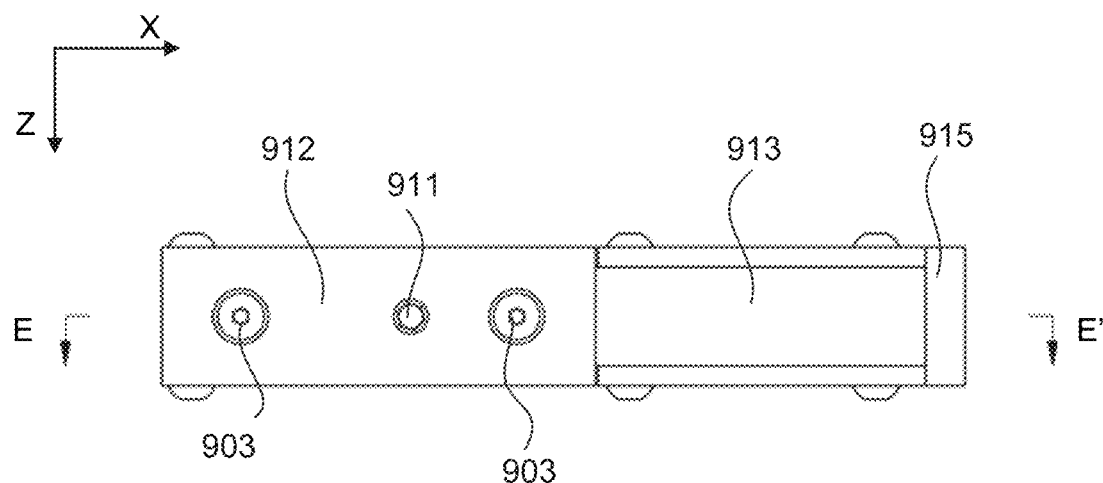
FIG. 9C illustrates a bottom view of an exemplary position adjustment device according to some embodiments of the present disclosure.
Figure 9D:
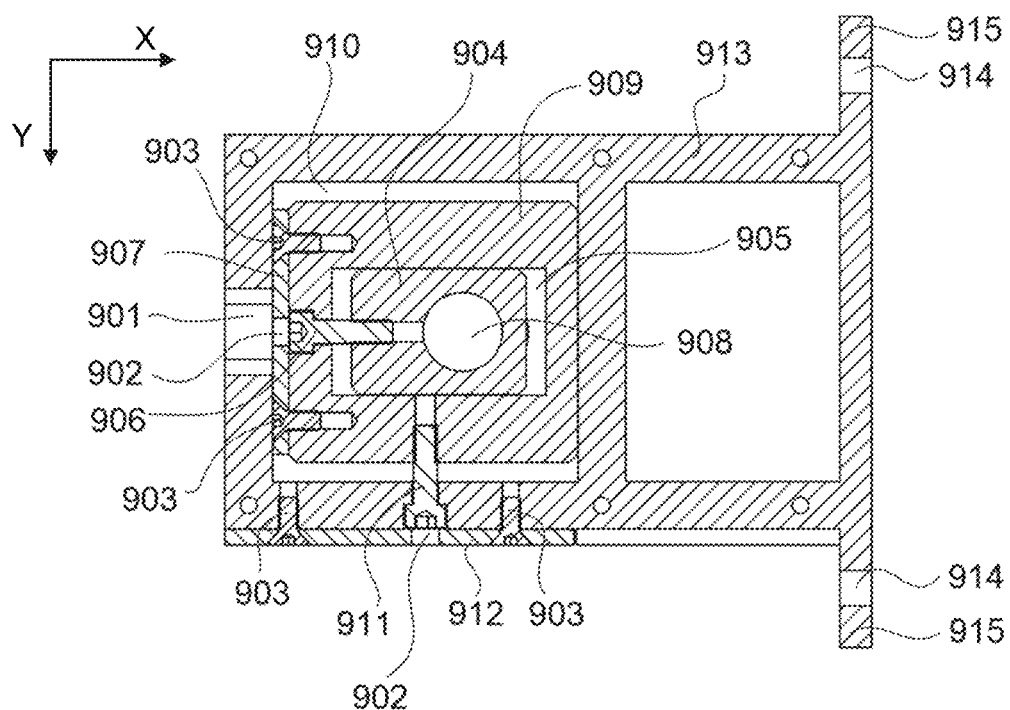
FIG. 9D illustrates a sectional view taken along E-E' of FIG. 9C according to some embodiments of the present disclosure.

FIG. 9C illustrates a bottom view of an exemplary position adjustment device 803 according to some embodiments of the present disclosure. The bottom view may be in an X-Z plane shown in FIG. 9A. As illustrated in FIG. 9C, the position adjustment device 803 may include one or more first adjustment holes 902 (not shown in FIG. 9C), a second adjustment piece 911, the second fastener 912, the housing 913, and a protruding end 915. In some embodiments, one or more screws 903 may be located in the first adjustment holes 902. The first adjustment holes 902 may be formed on a fastener (e.g., the second fastener 912).

FIG. 9D illustrates a sectional view taken along E-E' of FIG. 9C according to some embodiments of the present disclosure. The sectional view may be in the X-Y plane shown in FIG. 9A. As illustrated in FIG. 9D, the position adjustment device 803 may include one or more second adjustment holes 901, the first adjustment holes 902, one or more screws 903, a first moving piece 904, a first sliding cavity 905, the first adjustment piece 906, a first fastener 907, the fixed hole 908, a second moving piece 909, a second sliding cavity 910, the second adjustment piece 911, the second fastener 912, the housing 913, the sliding holes 914, and the protruding end(s) 915. The position adjustment device 803 may be configured to connect a first component (not shown in the FIG. 9D) and a second component (not shown in the FIG. 9D). Merely by way of example, the position adjustment device 803 may be mounted on the first component, and the first moving piece 904 of the position adjustment device 803 may be fixed onto or otherwise mechanically connected to the second component.

The first adjustment piece 906 may be mechanically connected to the first moving piece 904 and adjust the position of the first moving piece 904. The second adjustment piece 911 may be mechanically connected to the second moving piece 909 and adjust the position of the second moving piece 909. The second moving piece 909 may be mechanically connect to the first moving piece 904. The first adjustment piece 906 may adjust the position of the first moving piece 904 by causing the first moving piece 904 to move along a first direction. The first component may be driven by the first moving piece 904 and move accordingly (e.g., along the first direction). The second adjustment piece 911 may adjust the position of the second moving piece 909 by causing it to move along a second direction. The first moving piece 904 may be driven by the second moving piece 909 and move accordingly (e.g., along the second direction). The first moving piece 904 may be caused to move along the first direction only, the second direction only, a third direction only, or two or three of the first direction, the second direction, and the third direction. In some embodiments, the first direction may be the X axis direction, and the second direction may be the Y axis direction.

The first sliding cavity 905 may be configured to allow the first moving piece 904 to move along the first direction (e.g., the X axis direction). The first sliding cavity 905 may be located within the second moving piece 909. In some embodiments, the first sliding cavity 905 may have the shape of a cuboid. Accordingly, the first moving piece 904 may be a cuboid. The first moving piece 904 may move in the first sliding cavity 905 along one direction. The second sliding cavity 910 may be configured to allow the second moving piece 909 to move along the second direction (e.g., the Y axis direction). The second sliding cavity 910 may be configured in the housing 913.

In some embodiments, the first adjustment piece 906 may be a screw engaged in the second moving piece 909. In some embodiments, the screw may include a hexagon socket head cap screw. The first adjustment piece 906 and the first moving piece 904 may be connected by way of, e.g., a threaded engagement. The first moving piece 904 may be caused to move in the first sliding cavity 905 along the first direction by adjusting the screw.

The first fastener 907 may hold the first adjustment piece 906 in place in the second moving piece 909 and prevent the first adjustment piece 906 from falling out of the second moving piece 909. In some embodiments, the first fastener 907 may be a sheet. The sheet may be made of a metal material, for example, iron, copper, etc., or an alloy thereof. The sheet may be fixed on the second moving piece 909 via the screw 903. In some embodiments, the first fastener 907 may have one or more first adjustment holes 902. A screwdriver may pass through the first adjustment holes 902, and reach and adjust the first adjustment piece 906 (e.g., a hexagon socket head cap screw). The diameter of the first adjustment holes 902 may be less than the first adjustment piece 906 (e.g., the hexagon socket head cap screw). For instance, the diameter of the first adjustment hole 902 may be less than the diameter of the hexagon socket head of the first adjustment piece 906. Accordingly, the first adjustment piece 906 may be hold in place in the second moving piece 909.

Similarly, the second adjustment piece 911 may be a screw. In some embodiments, the screw may include a hexagon socket head cap screw. In some embodiments, the second fastener 912 may hold the second adjustment piece 911 in place in the housing 913 and prevent the second adjustment piece 911 from falling out of the housing 913. The second fastener 912 may be fixed on the housing 913 via the screw 903. In some embodiments, the second fastener 912 may have one or more first adjustment holes 902. The diameter of the first adjustment holes 902 may be less than the second adjustment piece 911 (e.g., the hexagon socket head cap screw). For instance, the diameter of the first adjustment hole 902 may be less than the diameter of the hexagon socket head of the second adjustment piece 911. Accordingly, the second adjustment piece 911 may be hold in place in the housing 913.

The housing 913 may have one or more second adjustment holes 901. A second adjustment hole 901 may be configured to provide passage space for a tool (e.g., a screwdriver) to access and adjust, from the outside of the housing 913, the first adjustment piece 906 by causing the first adjustment piece 906 to move along the X axis direction. In some embodiments, the dimension of a second adjustment hole 901 in the second direction may be greater than the largest distance that the second moving piece 909 is allowed to move along the second direction (e.g., the Y axis direction). Accordingly, the first adjustment piece 906 engaged or nested in the second moving piece 909 is movable along the Y axis direction by causing the second moving piece 909 to move. In some embodiments, the housing 913 may be regarded as a third moving piece and may move along a third direction. The third direction may be the Z axis direction shown in FIG. 9A.

For illustration purposes, an adjustment process of the position adjustment device 803 is provided. The position adjustment device 803 may be configured to connect a front cover plated (e.g., the front cover plate 801 in FIG. 8A) and a gantry (e.g., the gantry 802 in FIG. 8A). For example, the position of the front cover plate may be adjusted along the X axis direction by adjusting the first adjustment piece 906. The first adjustment piece 906 may drive the first moving piece 904 to move. Accordingly, the movement of the first moving piece 904 may drive the front cover plate to move along the X axis direction. As another example, the position of the front cover plate may be adjusted along the Y axis direction by adjusting the second adjustment piece 911. The second adjustment piece 911 may drive the second moving piece 909 to move. The movement of the second moving piece 909 may drive the first moving piece 904 to move. Accordingly, the movement of the first moving piece 904 may drive the front cover plate to move along the Y axis direction. As still another example, the position of the front cover plate may be adjusted along the Z axis direction (as illustrated in FIG. 9A) by moving the third moving piece (i.e., the housing 913) along the vertical axis of the sliding hole 914 (i.e., the Z axis). The movement of the housing 913 may drive the second moving piece 909 to move. The movement of the second moving piece 909 may drive the first moving piece 904 to move. Accordingly, the movement of the first moving piece 904 may drive the front cover plate to move along the Z axis. In some embodiments, before the housing 913 is moved, the screw(s) inserted into the sliding holes 914 may need to be loosened. In some embodiments, the position of the front cover plate may be adjusted in more than one direction by the coordination of at least two components of the first adjustment piece 906, the second adjustment piece 911, the first moving piece 904, the second moving piece 909, or the housing 913.

Figure 10:
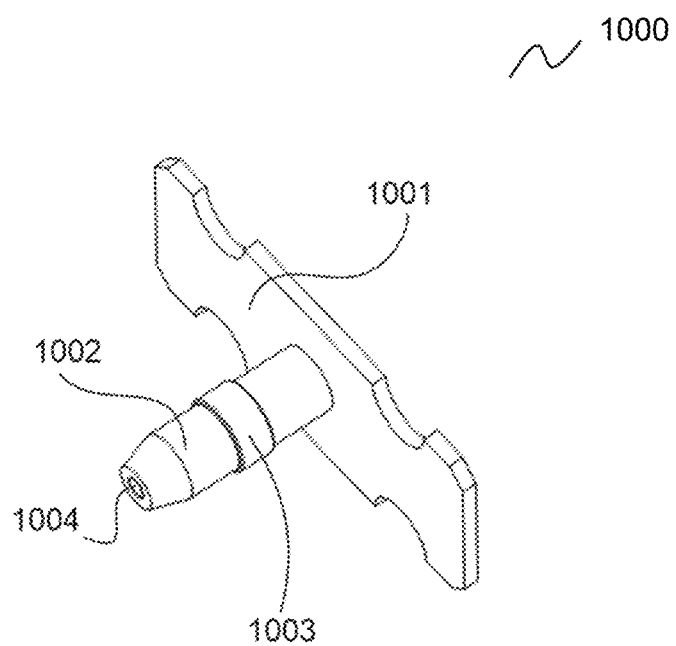
FIG. 10 illustrates an exemplary fixed pin according to some embodiments of the present disclosure.

FIG. 10 illustrates an exemplary fixed pin 1000 according to some embodiments of the present disclosure. The fixed pin 1000 may be configured to mechanically connect two components. For instance, the fixed pin 1000 may mechanically connect the first moving piece 904 of the position adjustment device 803 with another component (e.g., the gantry 802). As illustrated, the fixed pin 1000 may include a fixed plane 1001 and a pin 1002. The pin 1002 may include a fixed ring 1003 and a screw hole 1004. With reference to the example in which the fixed pin 1000 is used to mechanically connect the first moving piece 904 of the position adjustment device 803 with the gantry 802, the fixed plane 1001 may contact a surface of the gantry 802. The pin 1002 may be inserted into the fixed hole 908 of the position adjustment device 803. The fixed ring 1003 may be configured as a limit piece to limit the insertion depth of the pin 1002 into the fixed hole 908. Additionally, a screw corresponding to the screw hole 1004 may be used to fix the fixed pin 1000 on the position adjustment device 803. In some embodiments, the first moving piece 904 and the fixed pin 1000 may be configured as an integral piece. It should be noted that the description above is merely an example of a connection between the first moving piece 904 of the position adjustment device 803 with another component, and is not intended to be limiting.

Figure 11A:
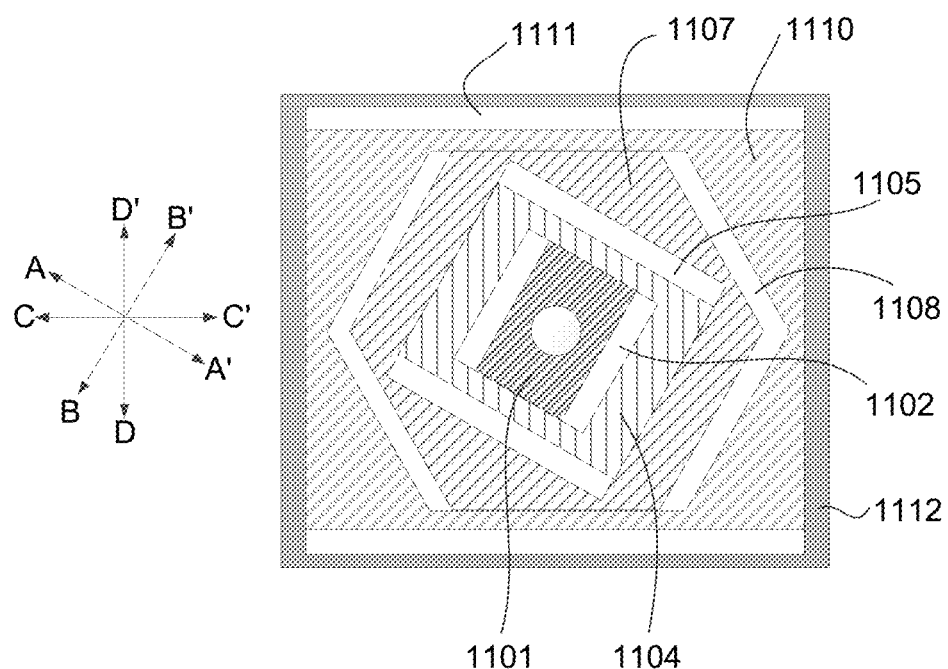
FIG. 11A illustrates an exemplary position adjustment device according to some embodiments of the present disclosure.

FIG. 11A illustrates an exemplary position adjustment device 803 according to some embodiments of the present disclosure. The position adjustment device 803 may include one or more sliding cavities and one or more moving pieces. In some embodiments, the position adjustment device 803 may adjust the relative position between the first component and the second component in various directions. A moving piece may be nested within another moving piece. A moving piece and another moving piece nested therein may be mechanically connected via an adjustment piece such that the two moving pieces may move relative to each other along a certain direction. As illustrated in FIG. 11A, the position adjustment device 803 may include a first moving piece 1101, a first sliding cavity 1102, a second moving piece 1104, a second sliding cavity 1105, a third moving piece 1107, a third sliding cavity 1108, a fourth moving piece 1110, a fourth sliding cavity 1111, and a fifth moving piece 1112. The first moving piece 1101 may move along a direction AA' in the first sliding cavity 1102 located inside the second moving piece 1104. The second moving piece 1104 may move along a direction BB' in the second sliding cavity 1105 located inside the third moving piece 1107. The third moving piece 1107 may move along a direction CC' in the third sliding cavity 1108 located inside the fourth moving piece 1110. The fourth moving piece 1110 may move along a direction DD' in the fourth sliding cavity 1111 located inside the fifth moving piece 1112.

Figure 11B:
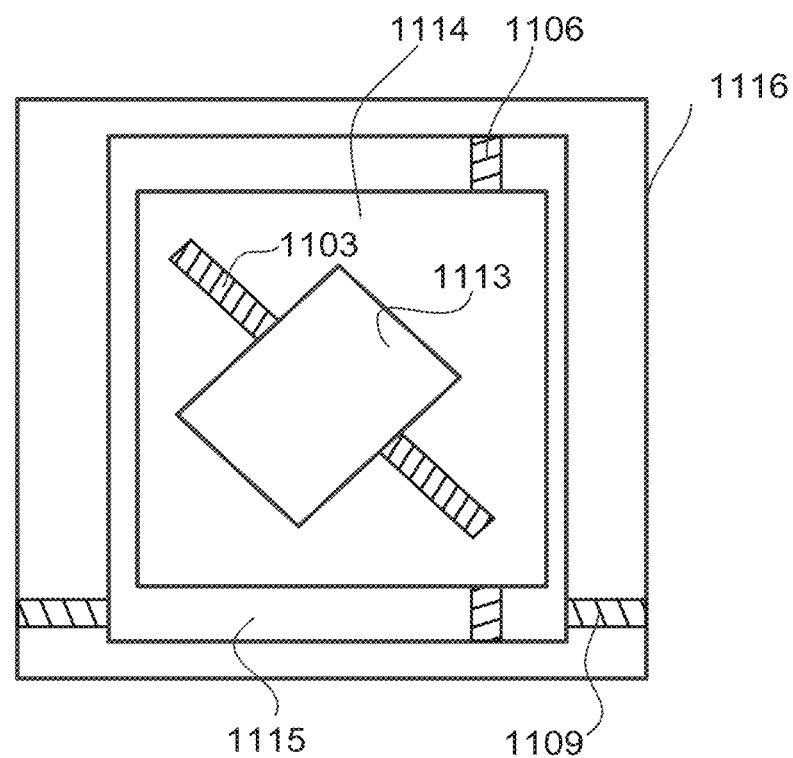
FIG. 11B illustrates an exemplary position adjustment device according to some embodiments of the present disclosure.

FIG. 11B illustrates an exemplary position adjustment device 803 according to some embodiments of the present disclosure. The position adjustment device 803 may include one or more sliding rails and one or more moving pieces. A moving piece may be nested within another moving piece. A moving piece and another moving piece nested therein may be mechanically connected via an adjustment piece such that the two moving pieces may move relative to each other along a certain direction. In some embodiments, an adjustment piece may be a sliding rail. As illustrated in FIG. 11B, the position adjustment device 803 may include a first moving piece 1113, a first sliding rail 1103, a second moving piece 1114, a second sliding rail 1106, a third moving piece 1115, a third sliding rail 1109, and a fourth moving piece 1116. The first moving piece 1113 may move along the first sliding rail 1103 configured on a side of the second moving piece 1114. The second moving piece 1114 may move along the second sliding rail 1106 configured on a side of the third moving piece 1115. The third moving piece 1115 may move along a third sliding rail 1109 configured on a side of the fourth moving piece 1116. In some embodiments, a sliding rail may be configured on an upper side, a bottom side, a left side, a right side, a front side, a rear side, an interior side, an exterior side, etc., of a moving piece.

It should be noted that the description in FIGS. 11A and 11B is merely an example of the position adjustment device 803, and is not intended to be limiting. For example, the position adjustment device 803 may be configured with a plurality of sliding cavities or sliding rails. For purposes of illustration, the position adjustment device 803 may include N moving pieces and N adjustment pieces corresponding to the N moving pieces. The N moving pieces may move along N directions. The nth moving piece (n is equal to or lower than N) may be connected to the (n−1)th moving piece. The nth moving piece may move along an nth direction with the assistance of an nth adjustment piece. At the same time, the (n−1)th moving piece may be driven to move along the nth direction. The number N may be a positive integer not less than 2. As another example, the position adjustment device 803 may be configured with a plurality of sliding cavities and a plurality of sliding rails. Merely by way of example, the position adjustment device 803 may include M sliding cavities and (N−M) sliding rails. The number M may be a positive integer less than or equal to N.

Figure 12A:
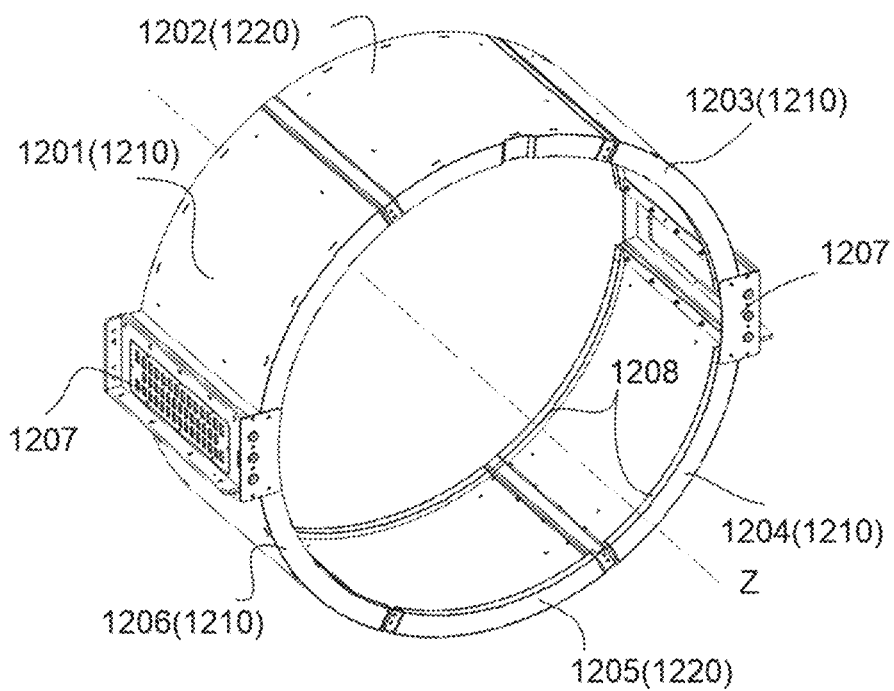
FIG. 12A illustrates an exemplary detector cover according to some embodiments of the present disclosure.

FIG. 12A illustrates an exemplary detector cover 320 according to some embodiments of the present disclosure. In some embodiments, the detector cover 320 may include one or more sub detector covers. FIG. 12C illustrates a top view of the detector cover 320 shown in FIG. 12A according to some embodiments of the present disclosure. As illustrated in FIGS. 12A and 12C, the detector cover 320 may include a first sub detector cover 1201, a second sub detector cover 1202, a third sub detector cover 1203, a fourth sub detector cover 1204, a fifth sub detector cover 1205, a sixth sub detector cover 1206, one or more data and power interfaces 1207, and a flanging structure 1208. In some embodiments, at least two of the sub detector covers of the detector cover 320 may have a same or similar structure. In some embodiments, at least two of the sub detector covers of the detector cover 320 may have different structures. For instance, the first sub detector cover 1201, the third sub detector cover 1203, the fourth sub detector cover 1204, and the sixth sub detector cover 1206 may have a similar structure, designated as a first-type sub detector cover 1210; the second sub detector cover 1202 and the fifth sub detector cover 1205 may have a similar structure, designated as a second-type sub detector cover 1220. The first-type sub detector cover 1210 may be the same as, similar to, or different from the second-type sub detector cover 1220.

The flanging structure 1208 may be located at a side wall of the detector cover 320 along the Z axis of the detector cover 320. In the side wall of the detector cover 320, the long axis of the flanging structure 1208 may be in a direction from a front end (see the arrow labeled as "FE" in FIG. 12C) to a back end (see the arrow labeled as "BE" in FIG. 12C) of the detector cover 320. The Z axis here may be the same as that illustrated in FIG. 9A. The flanging structure 1208 at the front end may facilitate the mounting of the detector cover 320 onto the main gantry 211 of a medical imaging device (e.g., a PET device), and the flanging structure 1208 at the back end may facilitate the mounting of the detector cover 320 on the back cover plate of the medical imaging device. In some embodiments, the main gantry, the detector cover 320, the back cover plate, and/or a sidewall of the scanning channel may encompass the detector support 330. In some embodiments, the detector cover 320 may form an isolated space surrounding the detector module 310. The isolated space may be separate from the space between the detector cover 320 and the cover plate 220 of the gantry assembly 111. In some embodiments, the isolated space may assist to improve the cooling efficiency of the cooling assembly 113.

Figure 12B:
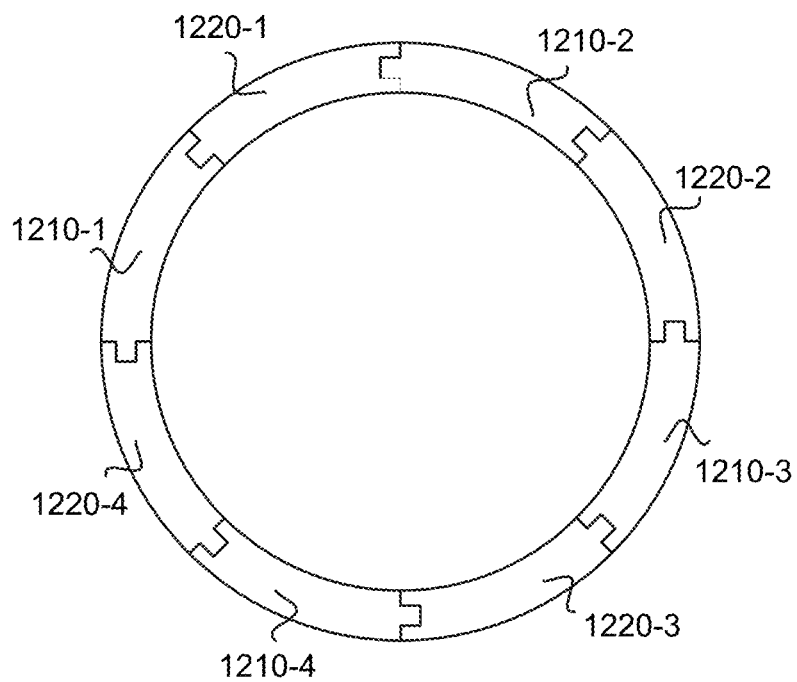
FIG. 12B illustrates an exemplary detector cover according to some embodiments of the present disclosure.
Figure 12C:
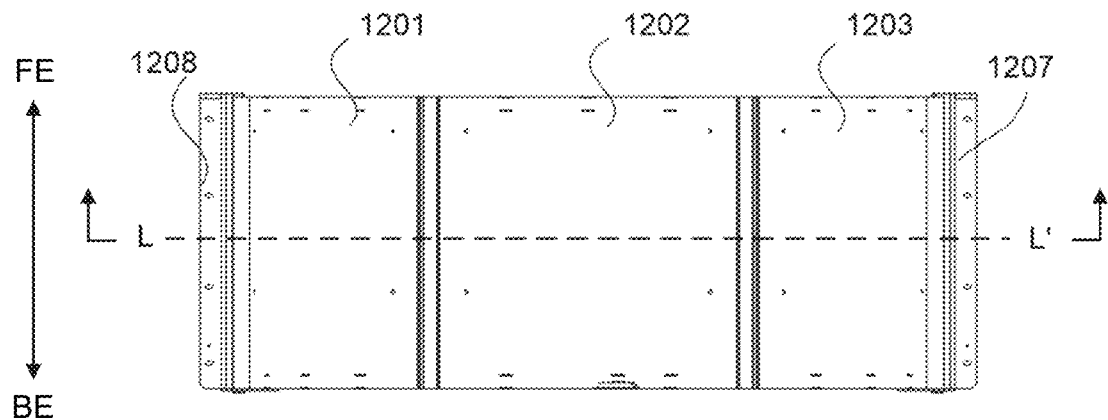
FIG. 12C illustrates a top view of the detector cover shown in FIG. 12A according to some embodiments of the present disclosure.

FIG. 12B illustrates an exemplary detector cover 320 according to some embodiments of the present disclosure. The detector cover 320 may include one or more first-type sub detector covers 1210 and one or more second-type sub detector covers 1220. In some embodiments, the first-type sub detector cover 1210 and the second-type sub detector cover 1220 may have the same or similar structure. In some embodiments, the first-type sub detector cover 1210 and the second-type sub detector cover 1220 may have different structures. In some embodiments, the second-type sub detector cover 1220 may fill the space between the first-type sub detector cover 1210 such that the detector cover 320 maintains a desirable shape (e.g., the shape of a circle, an ellipse, a polygon, etc.). In some embodiments, the second-type sub detector cover 1220 may be held in place by one or more first-type sub detector covers 1210. In some embodiments, the first-type sub detector cover 1210 may be fixed on the gantry. Merely by way of example, the first-type sub detector cover 1210 may be fixed on the gantry via one or more screws. The second-type sub detector cover 1220 may be connected to the first-type sub detector cover 1210. The connection between the second-type sub detector cover 1220 and the first-type sub detector cover 1210 may be formed by way of overlapping, mortise, occlusion, engagement, or the like, or any combination thereof.

In some embodiments, one sub detector cover in every few sub detector covers (e.g., every other sub detector cover, one in every three sub detector cover, etc.) may be fixed on the gantry, regardless of its type being the first-type sub detector cover 1210 or the second-type sub detector cover 1220. For illustration purposes, a detector cover including the first-type sub detector cover(s) 1210 and the second-type sub detector cover(s) 1220 is used below as an example. In some embodiments, the detector cover 320 may include n first-type sub detector covers 1210 (e.g., a first first-type sub detector cover 1210-1, a second first-type sub detector cover 1210-2, a third first-type sub detector cover 1210-3, a fourth first-type sub detector cover 1210-4, . . . , an nth first-type sub detector cover 1210-n) and n second-type sub detector covers 1220 (e.g., a first second-type sub detector cover 1220-1, a second second-type sub detector cover 1220-2, a third second-type sub detector cover 1220-3, a fourth second-type sub detector cover 1210-4, . . . , an nth second-type sub detector cover 1220-n). In some embodiments, a first-type sub detector cover 1210 may have a stripe shape with two ends, each end of which includes a bulge and a groove. A second-type sub detector cover 1220 may have a stripe shape with two ends, each of which includes a bulge and a groove. In some embodiments, the first first-type sub detector cover 1210-1 may be fixed on the gantry. The bulge of the first second-type sub detector cover 1220-1 may be inserted into the groove of the first first-type sub detector cover 1210-1. The bulge of the second first-type sub detector cover 1210-2 may then be inserted into the groove of the first second-type sub detector cover 1220-1. The bulge of an nth second-type sub detector cover 1220-n may be inserted into the groove of an nth first-type sub detector cover 1210-n. Similarly, the bulge of the first first-type sub detector cover 1210-1 may be inserted into the groove of the nth second-type sub detector cover 1220-n. In this way, the assembly and disassembly of the detector cover 320 may be facilitated.

Figure 12D:
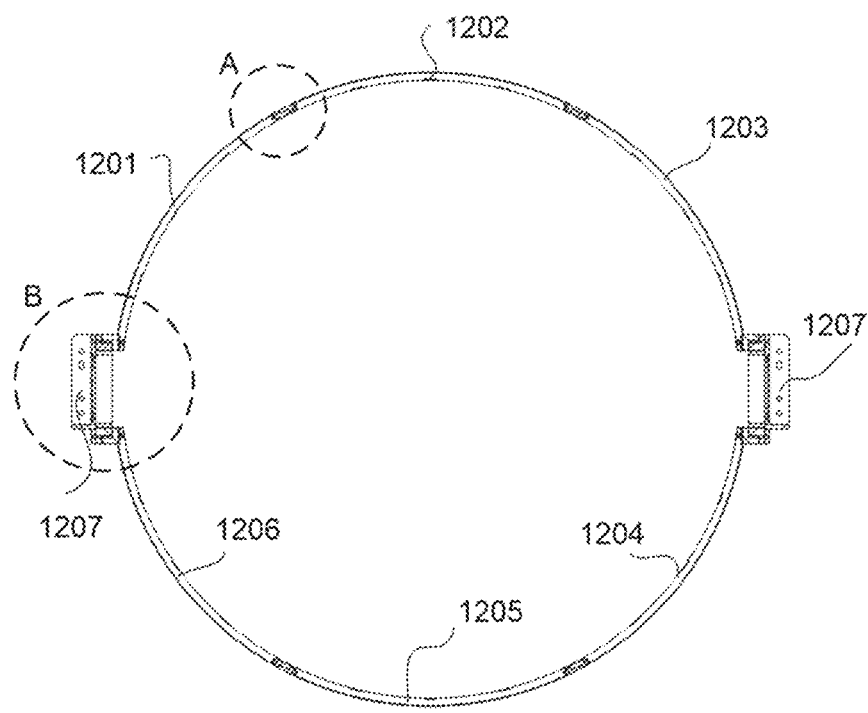
FIG. 12D illustrates a sectional view from L-L' of FIG. 12C according to some embodiments of the present disclosure.

FIG. 12D illustrates a sectional view from L-L' of FIG. 12C according to some embodiments of the present disclosure. As illustrated, the detector cover 320 may include four first-type sub detector covers (the first sub detector cover 1201, the third sub detector cover 1203, the fourth sub detector cover 1204, and the sixth sub detector cover 1206), two second-type sub detector covers (the second sub detector cover 1202 and the fifth sub detector cover 1205), and two data and power interfaces 1207. In some embodiments, the structures and/or sizes of the six sub detector covers may be the same or different. If the structures and sizes of the four first-type sub detector covers are the same, the four first-type sub detector covers may be used interchangeably. Similarly, if the structures and sizes of the two second-type sub detector covers are the same, the two second-type of sub detector covers may be used interchangeably. In some embodiments, the detector cover 320 may include six sub detector covers, and the second-type sub detector covers may include a top sub detector cover (e.g., the second sub detector cover 1202) and/or a bottom sub detector cover (e.g., the fifth sub detector cover 1205). In some embodiments, a plurality of first-type sub detector covers and a plurality of second-type sub detector covers may be arranged alternately.

In some embodiments, the first sub detector cover 1201 and the third sub detector cover 1203 may be fixed firstly to assemble the detector cover 320. The second sub detector cover 1202 may then be placed in a corresponding position between the first sub detector cover 1201 and the third sub detector cover 1203. The assembly process may be repeated with respect to the fourth sub detector cover 1204, the fifth sub detector cover 1205, and the sixth sub detector cover 1206. A first data and power interface 1207 may be assembled between the first sub detector cover 1201 and the sixth sub detector cover 1206. A second data and power interface 1207 may be assembled between the third sub detector cover 1203 and the fourth sub detector cover 1204. The region A shown in FIG. 12D may include a connection between a first-type sub detector cover (e.g., the first sub detector cover 1201) and a second-type sub detector cover (e.g., the second sub detector cover 1202). The region B shown in FIG. 12D may include a connection between a data and power interface 1207 and two first-type sub detector covers (e.g., the first sub detector cover 1201 and the sixth sub detector cover 1206). More descriptions regarding the region A and the region B may be found elsewhere in the present disclosure. See, e.g., FIGS. 13A and 13B and the description thereof. It should be noted that the detector cover 320 shown in FIGS. 12A through 12D may be the same as or different from the detector cover 504 shown in FIG. 5A, the detector cover 606 shown in FIG. 6B, the detector cover 618 shown in FIG. 6D, and/or the detector cover 701 shown in FIG. 7A.

Figure 13A:
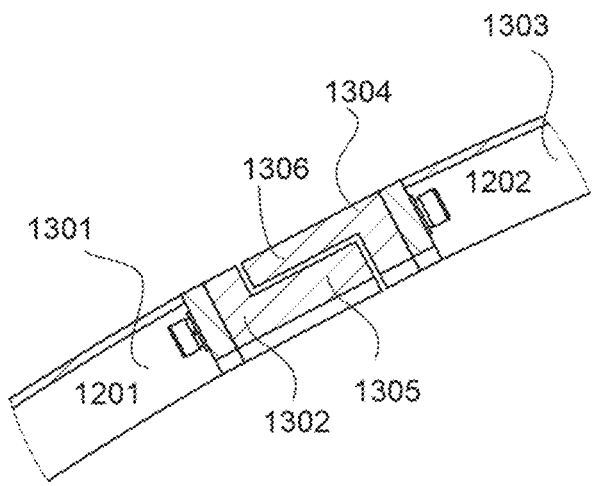
FIG. 13A illustrates an enlarged view of the region A shown in FIG. 12D according to some embodiments of the present disclosure.

FIG. 13A illustrates an enlarged view of the region A shown in FIG. 12D according to some embodiments of the present disclosure. As illustrated, the first sub detector cover 1201 may include a first curved piece 1301 and two connecting pieces (e.g., a first connecting piece 1302 and a second connecting piece 1307 (see FIG. 13B)). The two connecting pieces may be arranged on two ends of the first curved piece 1301, respectively. The first curved piece 1301 and the first connecting piece 1302 may be connected via one or more screws. The first connecting piece 1302 may have an "L" shape. Similarly, the second sub detector cover 1202 may include a second curved piece 1303 and one or more connecting pieces (e.g., a third connecting piece 1304 and a fourth connecting piece (not shown)). The first connecting piece 1302 may include a first long arm 1305. The third connecting piece 1304 may include a second long arm 1306. The first curved piece 1301 and the second curved piece 1303 may be the same or different. If the first curved piece 1301 and the second curved piece 1303 are the same, the first curved piece 1301 and the second curved piece 1303 may be used interchangeably. The first connecting piece 1302 and the third connecting piece 1304 may be the same or different. If the first connecting piece 1302 and the third connecting piece 1304 are the same, the first connecting piece 1302 and the third connecting piece 1304 may be used interchangeably.

The first sub detector cover 1201 and the second sub detector cover 1202 may be connected via the connection between the first connecting piece 1302 and the third connecting piece 1304. The connection between the connecting piece 1302 and the connecting piece 1303 may be formed by way of overlapping, mortise, occlusion, engagement, and the like. In some embodiments, the first connecting piece 1302 and the third connecting piece 1304 may have complementary structures such that the first sub detector cover 1201 and the second sub detector cover 1202 may be connected by forming an overlap. For example, the orientations of the first long arm 1305 and the second long arm 1306 may be opposite, and thus the connection between the first long arm 1305 and the second long arm 1306 may be formed by way of at least overlapping the first long arm 1305 and the second long arm 1306. It should be noted that other regions relating to a connection between a first sub detector cover and a second sub detector cover may be the same as the region A.

Figure 13B:
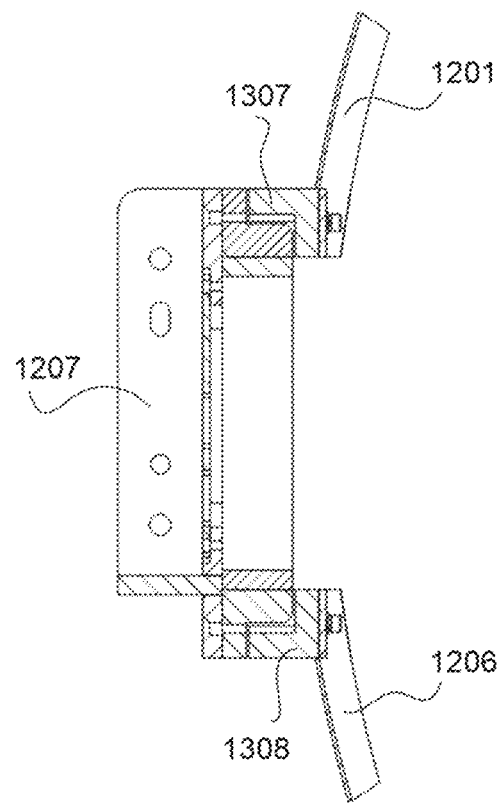
FIG. 13B illustrates an enlarged view of the region B shown in FIG. 12D according to some embodiments of the present disclosure.

FIG. 13B illustrates an enlarged view of the region B shown in FIG. 12D according to some embodiments of the present disclosure. As illustrated, a data and power interface 1207 may be connected to the first sub detector cover 1201 and the sixth sub detector cover 1206. The data and power interface 1207 may be connected to the first sub detector cover 1201 via the second connecting piece 1307. The data and power interface 1207 may be connected to the sixth sub detector cover 1206 via a fourth connecting piece 1308. The second connecting piece 1307 and the fourth connecting piece 1308 may have an "L" shape. It should be noted that other regions relating to a connection between a data and power interface and a sub detector cover may be the same as the region B.

Figure 14:
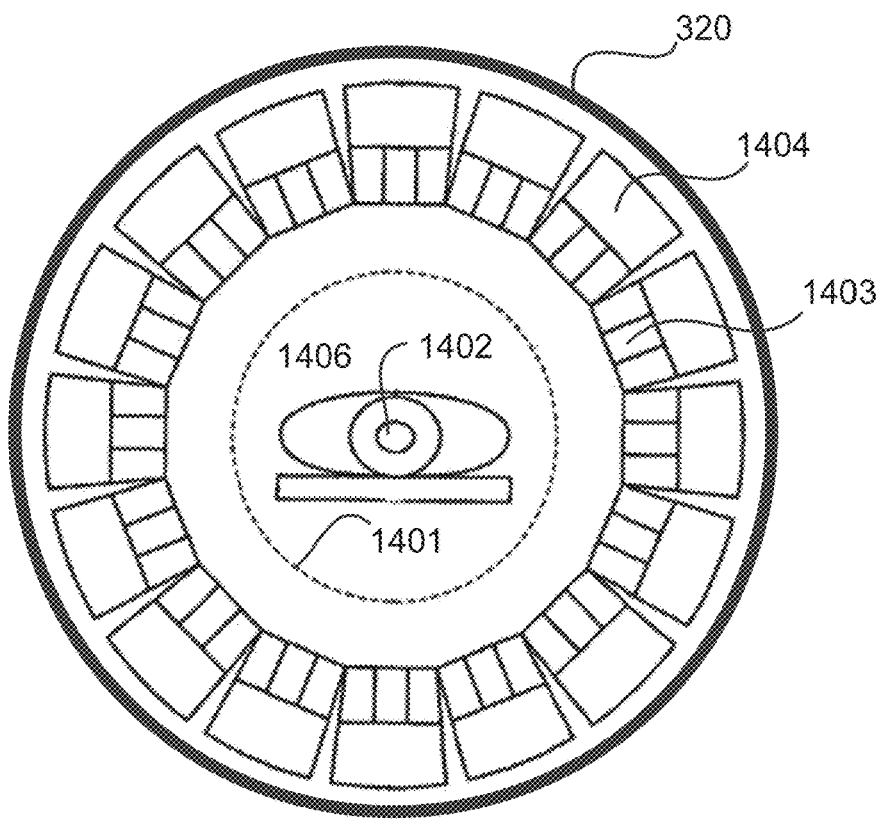
FIG. 14 illustrates a schematic front view of an exemplary scanner with a detector cover according to some embodiments of the present disclosure.

FIG. 14 illustrates a schematic front view of an exemplary scanner 110 with a detector cover 320 according to some embodiments of the present disclosure. As illustrated, the scanner 110 may include a scanning channel 1406, a sidewall 1401 of the scanning channel 1406, one or more detector modules 1403, one or more detector supports 1404, and a detector cover 320. In some embodiments, the detector modules 1403 may be the same as or different from the detector modules 519 shown in FIG. 5B, the detector modules 604 shown in FIG. 6A, the detector modules 612 shown in FIG. 6C, and/or the detector modules 711 shown in FIG. 7B. The detector cover 320 shown in FIG. 14 may be the same as or different from the detector cover 504 shown in FIG. 5A, the detector cover 606 shown in FIG. 6B, the detector cover 618 shown in FIG. 6D, and/or the detector cover 701 shown in FIG. 7A. The scanning channel 1406 may be the same as or different from the scanning channel 502 shown in FIG. 5A, the scanning channel 518 shown in FIG. 5B, the scanning channel 605 shown in FIG. 6A, the scanning channel 609 shown in FIG. 6B, the scanning channel 611 shown in FIG. 6C, and/or the scanning channel 616 shown in FIG. 6D. An object 1402 to be examined may be positioned in the scanning channel 1406. Merely by way of example, the scanner 110 is a PET scanner. The detector modules 1403 may be configured to detect gamma photons emitted by the object 1402. In some embodiments, the detector module(s) 1403 may be arranged around the scanning channel 1406 with the support by the detector support(s) 1404. The detector module(s) 1403 and/or the detector support(s) 1404 may be arranged in a circle, an ellipse, etc., around the scanning channel 1406.

The cover plates of the gantry and the detector module(s) 1403 may form a space. The detector cover 320 may be positioned between the cover plates and the detector module(s) 1403. Accordingly, a smaller space containing the detector module(s) 1403 may be formed and isolated from the remaining portion of the space. The smaller space may improve the cooling effect of the cooling assembly 113.

Figure 15:
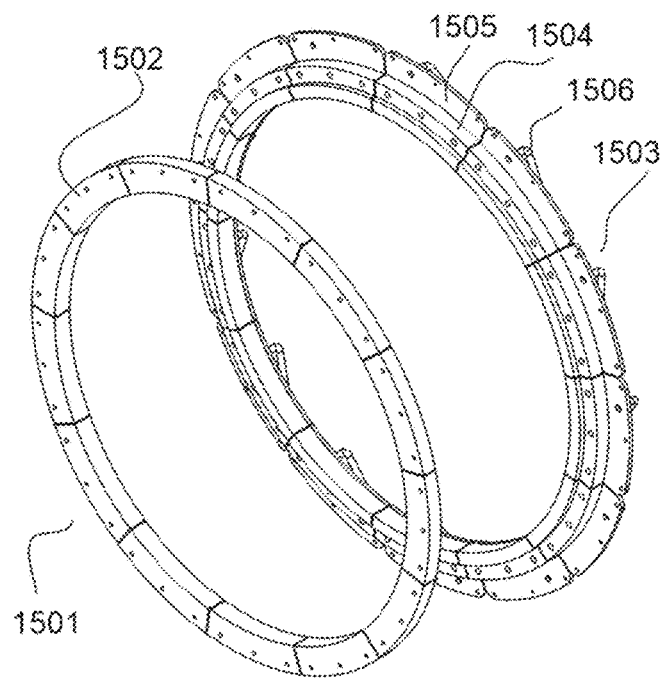
FIG. 15 illustrates an exemplary ring assembly according to some embodiments of the present disclosure.

FIG. 15 illustrates an exemplary ring assembly 332 according to some embodiments of the present disclosure. As illustrated in FIG. 15, the ring assembly 332 may include a first ring 1501 and a second ring 1503. In some embodiments, the first ring 1501 and the first ring 705 shown in FIG. 7B may be the same or different. In some embodiments, the second ring 1503 and the second ring 707 shown in FIG. 7B may be the same or different. The first ring 1501 may include one or more first segments 1502. The second ring 1503 may include one or more second segments 1504. The first segments 1502 and/or the second segments 1504 may have a curved shape. In some embodiments, each one of or both of the first ring 1501 and the second ring 1503 may further include a flange, respectively. More descriptions regarding the flange may be found elsewhere in the present disclosure. See, e.g., FIG. 7B and the description thereof. In some embodiments, the number of the first segments 1502 of the first ring 1501 may be in a range from 5 to 60. For example, the number of the first segments 1502 may be 5, 13, or any suitable number. In some embodiments, the number of the first segments 1502 of the first ring 1501 may be 1, i.e., the first ring 1501 may be an integral part. The number of the second segments 1504 of the second ring 1503 may be the same as or different from the number of the first segments 1502 of the first ring 1501. In some embodiments, the number of the second segments 1504 of the second ring 1503 may be in a range from 5 to 60.

In some embodiments, a second segment 1504 may further include a fixing brim 1505. In some embodiments, the fixing brim 1505 may extend from an outer edge of the second segment 1504. The fixing brim 1505 may be used to fix the second segment 1504 on a limit plate (e.g., the limit plate 515) via one or more screws. In some embodiments, the fixing brim 1505 and the second segment 1504 may be an integral piece. In some embodiments, the fixing brim 1505 and the second segment 1504 may be separate pieces connected together via a screw or welding. In some embodiments, a second segment 1504 may further include a handle 1506. The handle 1506 may be placed on a surface of the second segment 1504 away from the detector module(s) 310. The handle 1506 may have a "U" shape, a "T" shape, an "L" shape, any other suitable shape, or the like, or any combination thereof.

Figure 16:
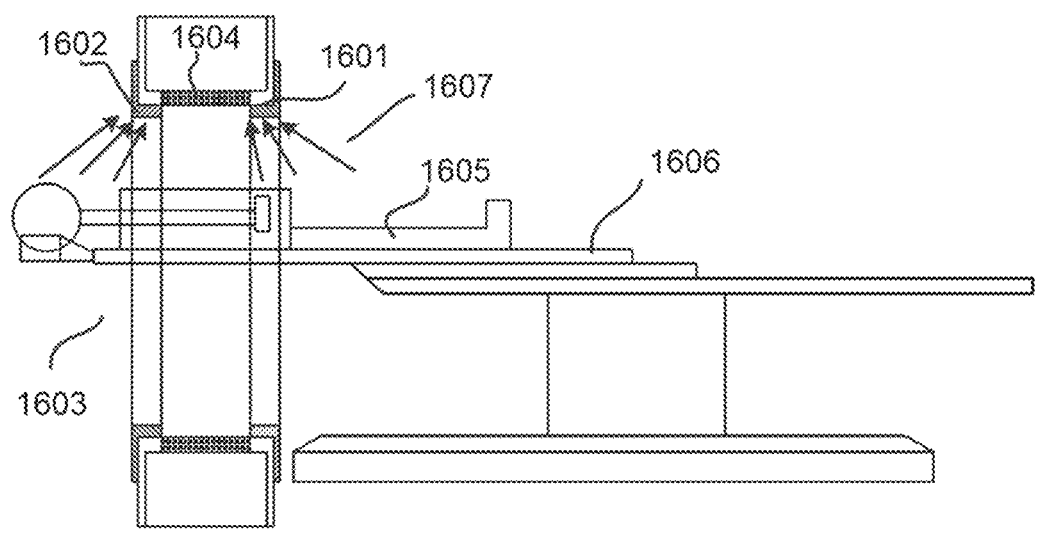
FIG. 16 illustrates a schematic configuration of an exemplary scanner with a ring according to some embodiments of the present disclosure.

FIG. 16 illustrates a schematic configuration of an exemplary scanner 110 with a ring according to some embodiments of the present disclosure. Merely by way of example, the scanner 110 is a PET scanner. As illustrated, an object 1605 (e.g., a patient) laying on a table 1606 may be positioned inside an imaging region of a scanning channel 1603. The imaging region may be defined by the scanning channel 1603 and one or more detector modules 1604. The scanning channel 1603 may be surrounded by the detector modules 1604 and one or more rings, for example, a first ring 1601, a second ring 1602. In some embodiments, the scanning channel 1603 and the scanning channel 518 shown in FIG. 5B may be the same or different. In some embodiments, the detector modules 1604 and the detector modules 711 shown in FIG. 7B may be the same or different. In some embodiments, the first ring 1601 and the first ring 1501 shown in FIG. 15 may be the same or different. In some embodiments, the second ring 1602 and the second ring 1503 shown in FIG. 15 may be the same or different. In some embodiments, the detector modules 1604 may have a first side and a second side along an axial direction of the scanning channel 1603, the first side may be closer to the front face of the scanning channel than the second side. In some embodiments, the first ring 1601 may be located on the first side of the detector modules 1604. In some embodiments, the second ring 1602 may be located on the second side of detector modules 1604.

Before imaging, a radioactive tracer isotope may be injected into the object 1605. The tracer isotope may include glucose, protein, nucleic acid, fatty acid labeled with short-lived radionuclides (e.g., F18, C11). Then gamma photons may be emitted from the object 1605. The gamma photons may be divided into two portions including a first portion and a second portion. The first portion may be desired gamma photons emitted by a part of the object 1605 in the imaging region. The second portion may be undesired gamma photons 1607 emitted by another part of the object 1605 out of the imaging region. The detector modules 1604 may detect the desired gamma photons and/or the undesired gamma photons 1607. The first ring 1601 and the second ring 1602 may block the undesired gamma photons 1607 from being detected by the detector modules 1604 such that the undesired gamma photons 1607 detected by the detector modules 1604 may be reduced and the accuracy of the scanner 110 may be improved.

Figure 17A:
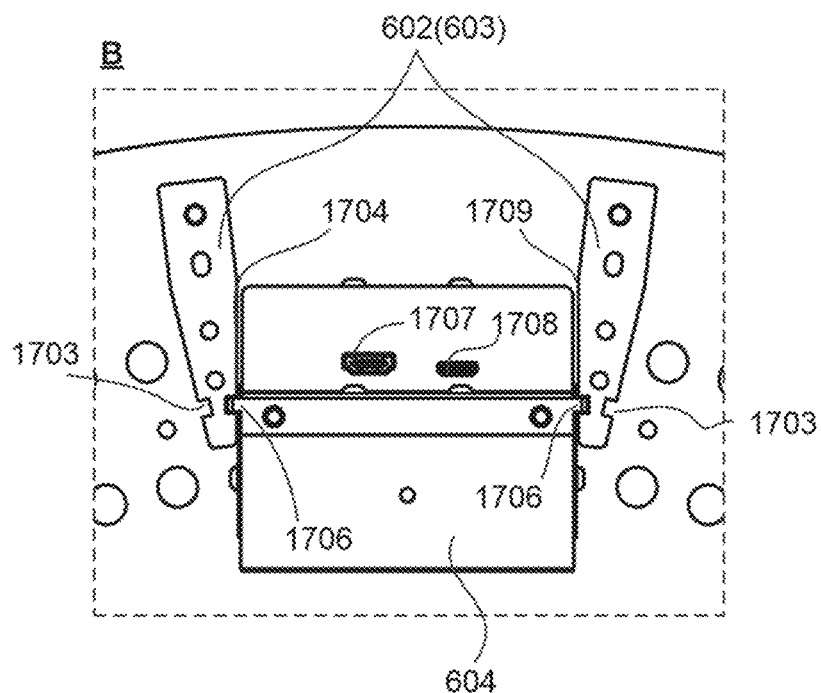
FIG. 17A illustrates an enlarged view of the region B shown in FIG. 6A according to some embodiments of the present disclosure.
Figure 17B:
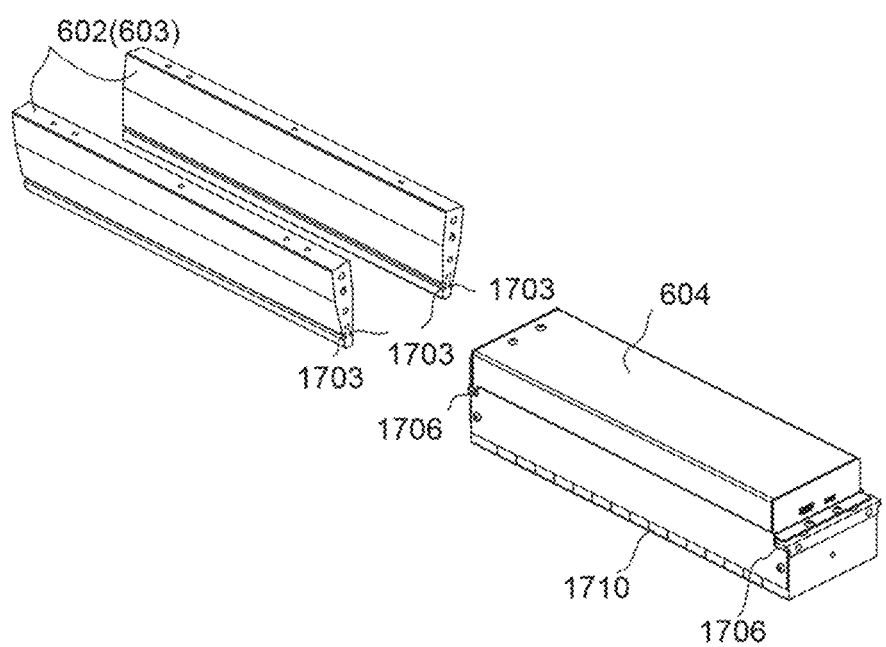
FIG. 17B illustrates an exemplary detector module and an exemplary guide plate according to some embodiments of the present disclosure.

FIG. 17A illustrates an enlarged view of the region B shown in FIG. 6A according to some embodiments of the present disclosure. FIG. 17B illustrates an exemplary detector module and an exemplary guide plate according to some embodiments of the present disclosure. As illustrated in FIG. 17A, a detector module 604 (including a detector 1710 illustrated in FIG. 17B) may be assembled between two adjacent guide plates 602 (e.g., a first guide plate and a second guide plate) or guide pieces 603 (or guide units 508). The detector 1710 may face the scanning channel to detect signals (e.g., gamma photons). The first guide plate and the second guide plate may be perpendicular or substantially perpendicular to the main gantry 601 and distributed along the radial direction of the scanning channel 605 and fixed via one or more screws and one or more fixed holes. The fixed holes may be located on the main gantry 601. In some embodiments, the detector module 604 may be configured as a cuboid. Accordingly, a first side 1704 and a second side 1709 of the detector module 604 may approach the two adjacent guide plates and be substantially parallel to the two adjacent guide plates.

The guide plates 602 may be configured with a guide rail on at least one side surface. The detector module 604 may be configured with one or more guide pieces corresponding to the guide rail(s). In some embodiments, the guide rail(s) and the corresponding guide plate(s) may form an integral part. In some embodiments, the guide rail(s) and the corresponding guide plate(s) may be separate parts and may be assembled together. In some embodiments, the guide rail(s) may be one or more groove(s) 1703. Correspondingly, the guide piece(s) of the detector module 604 may be the bulge(s) 1706 (also referred to as protrusion(s)). In some embodiments, the bulge(s) 1706 (also referred to as protrusion(s)) of a detector module 604 may be pushed into the groove(s) 1703 of the guide rail on a guide plate 602 to assemble the detector module 604 with the guide plate 602.

The detector module 604 may be configured with a data interface 1707 and a power interface 1708. The data interface 1707 may be configured to transmit data between the detector module 604 and one or more other devices. The power interface 1708 may provide an interface with a power supplier. In some embodiments, the data interface 1707 and/or the power interface 1708 may be configured on an end surface far away from a main mounting plate of the scanner 110. In some embodiments, the data interface 1707 and the power interface 1708 may be integrated into a data and power interface.

FIG. 18A illustrates an exemplary detector module 604 and an exemplary guide unit 508 according to some embodiments of the present disclosure. The guide unit 508 may be a guide plate 1804. One or more guide plates 1804 may be arranged along the circumference of the scanning channel 605. In some embodiments, the guide plates 1804 may be distributed evenly. A guide plate 1804 may have one or more limit sheets on the left side and/or right side of the guide plate 1804. The left side and/or the right side may be in a plane perpendicular or substantially perpendicular to the axial direction of the scanning channel 605. The limit sheets may be located at an end of the guide plate 1804 approaching the scanning channel 605. Accordingly, the detector module 604 may include one or more limit blocks corresponding to the limit sheets. In some embodiments, a limit sheet may be a hooking brim 1802, and the corresponding limit block may be a flange 1807. The flange 1807 of a detector module 604 may be pushed into the recess of the hooking brim 1802 of a guide plate 1804 to assemble the detector module 604 with the guide plate 1804. In some embodiments, a limit piece (e.g., the limit piece 509) may be fixed on the hooking brim 1802 via one or more screws. The limit piece may limit the movement of the detector module 604 in the axial direction of the scanning channel 605.

FIG. 18B illustrates an exemplary detector module 604 and an exemplary guide unit 508 according to some embodiments of the present disclosure. As illustrated in FIG. 18B, the connection between a detector module 604 and a guide unit 508 may be similar to that illustrated in FIG. 18A. The guide unit 508 may be a guide plate 1804. The connection between the detector module 604 and the guide unit 508 may be realized via a flange on the guide plate 1804 and a groove on the detector module 604. In some embodiments, the flange may be located on the guide plate 1804 instead of on the detector module 604, and the groove may be located on the detector module 604 instead of on the guide plate 1804.

FIG. 18C illustrates an exemplary detector module 604 and an exemplary guide unit 508 according to some embodiments of the present disclosure. The guide unit 508 may be a guide column 1803 configured along the circumference of the scanning channel 605 and perpendicular or substantially perpendicular to the main mounting plate. In some embodiments, the guide column 1803 and the main mounting plate may be configured as an integral part.

The detector module 604 may include one or more guide holes. In some embodiments, two guide columns 1803 may correspond to one detector module 604; accordingly, the detector module 604 may include two guide holes. In some embodiments, one guide column 1803 may correspond to one detector module 604; accordingly, the detector module 604 may include one guide hole. The guide columns 1803 may be pushed into corresponding guide holes to assemble the detector module 604 with the guide unit 508. In some embodiments, a screw hole 1806 may be provided at one end (away from the main mounting plate) of a guide column 1803. A limit piece 1801 (e.g., the limit piece 509) may be fixed on the guide column 1803 via a screw inserted into the screw hole(s) 1806. In some embodiments, the guide column 1803 may be a rectangular column, a triangular prism, an oval column, a cylinder, any other suitable column, or the like, or any combination thereof.

Figure 19A:
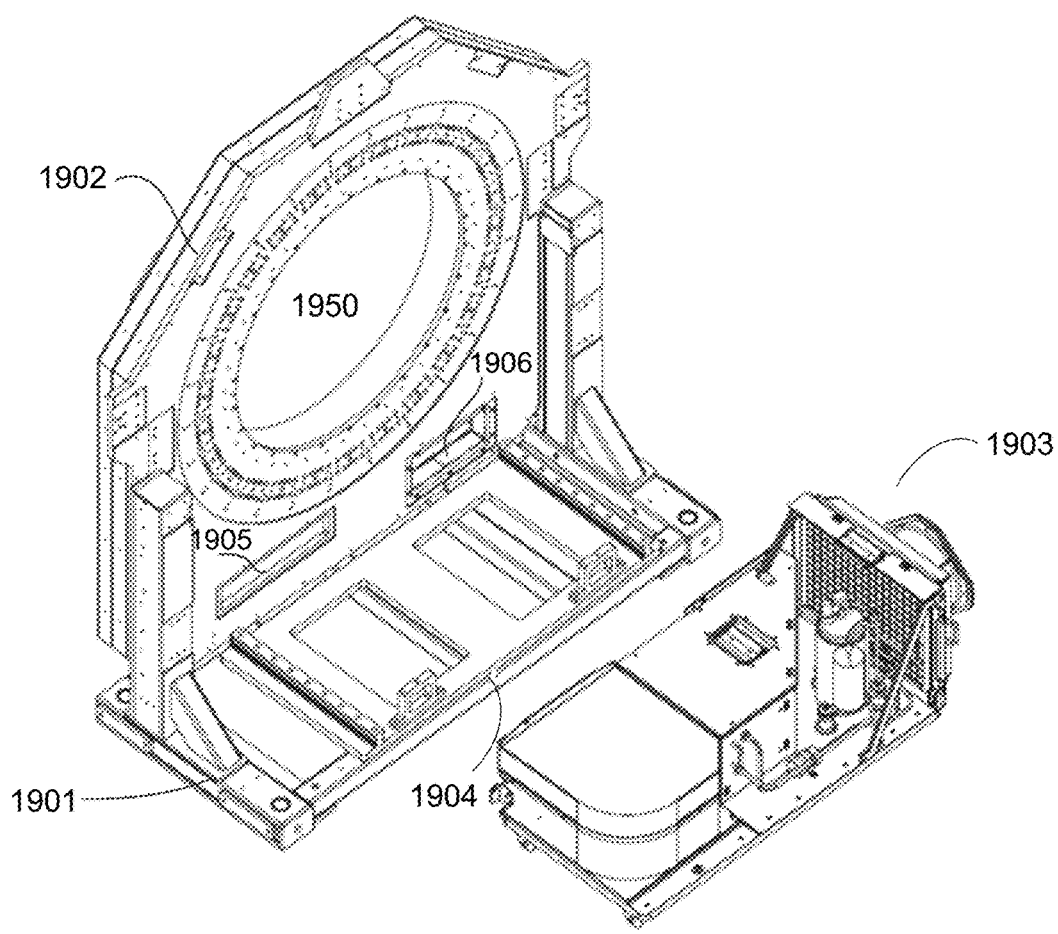
FIG. 19A illustrates a perspective view of an exemplary gantry and an exemplary sliding device of an imaging device (e.g., a PET device) according to some embodiments of the present disclosure.

FIG. 19A illustrates a perspective view of an exemplary gantry and an exemplary sliding device 1904 of an imaging device (e.g., a PET device) according to some embodiments of the present disclosure. The gantry (e.g., a PET gantry) may include a gantry base 1901 and a main gantry 1902. In some embodiments, the gantry base 1901 and the gantry base 608 shown in FIG. 6B may be the same or different. In some embodiments, the main gantry 1902 and the front cover plate 607 shown in FIG. 6B may be the same or different. An inlet chamber port 1905 and a return chamber port 1906 may be formed on the main gantry 1902. In some embodiments, the inlet chamber port 1905 and the inlet chamber port 620 shown in FIG. 6D may be the same or different. In some embodiments, the return chamber port 1906 and the return chamber port 622 shown in FIG. 6D may be the same or different. One or more detector modules (not shown in FIG. 19A) may be mounted on a detector support (not shown in FIG. 19A). The detector support may be assembled on the main gantry 1902. In some embodiments, the detector support may have a circular shape. In some embodiments, the opening of a scanning channel 1950 may be located above the gantry base 1901 by a certain distance, as illustrated in FIG. 19A. In some embodiments, a cooling device 1903 in the cooling assembly 113 may be supported on the gantry base 1901. In some embodiments, the cooling device 1903 may include one or more components of the cooling assembly 113 including, for example, a refrigerator 410, a compressor chamber 430, etc. The cooling assembly 113 may be used to cool one or more heat generating components of the imaging device including, for example, detector modules, electrical components, or the like. The cooling assembly 113 may cool the imaging device such that the temperatures of various portions of the imaging device are maintained at acceptable levels and the imaging device functions properly. In some embodiments, a cooling medium cooled by the cooling device 1903 may flow through the inlet chamber port 1905 and absorb heat from one or more heat generating components. Then the heated cooling medium may flow through the return chamber port 1906 and return to the cooling device 1903 to be cooled. This process may be repeated to cool the heat generating components of the imaging device.

As shown in FIG. 19A, the space for accommodating the cooling device 1903 on the gantry base 1901 may be relatively small. In some embodiments, it may be inconvenient for an engineer or technician to install, maintain, and/or disassemble the cooling device 1903 in such a small space, and it may reduce the work efficiency of the engineer or technician. In the present disclosure, a sliding device 1904 may be provided underneath the cooling device 1903. In some embodiments, the cooling device 1903 may be mounted on the sliding device 1904 in an open space outside the gantry (e.g., in a room where the imaging device is located), a space different from the space for accommodating the cooling device 1903 in the gantry. The sliding device 1904 may drive the cooling device 1903 to slide onto the gantry base 1901. The cooling device 1903 may be aligned with the inlet chamber port 1905 and the return chamber port 1906 to achieve a circulation of the cooling medium in the cooling assembly 113.

Figure 19B:
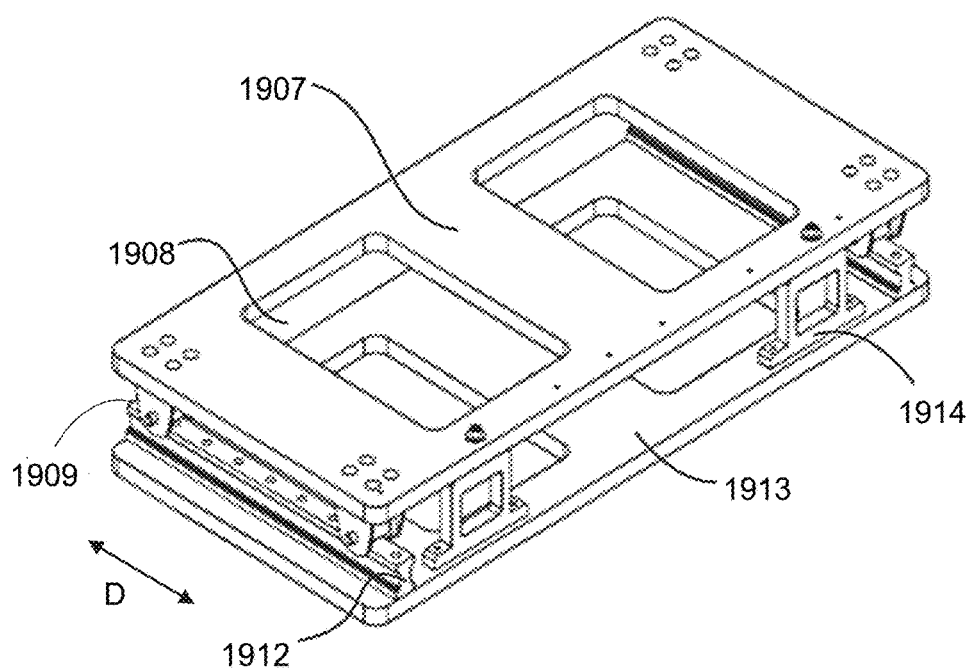
FIG. 19B illustrates a perspective view of an exemplary sliding device according to some embodiments of the present disclosure.
Figure 19C:
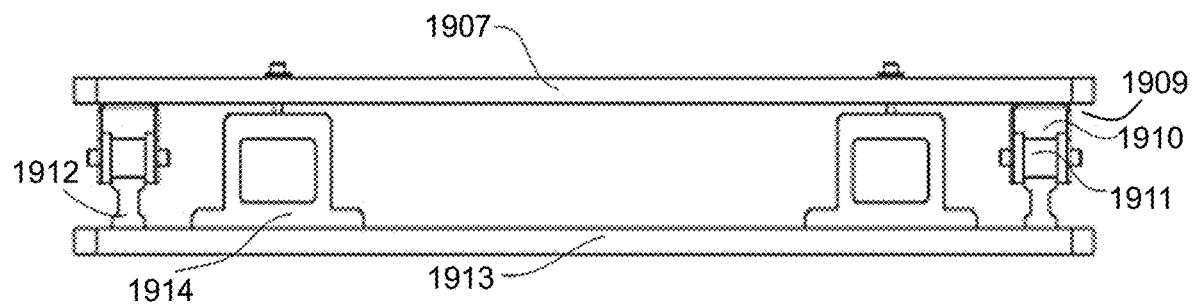
FIG. 19C illustrates a front view of an exemplary sliding device according to some embodiments of the present disclosure.
Figure 19D:
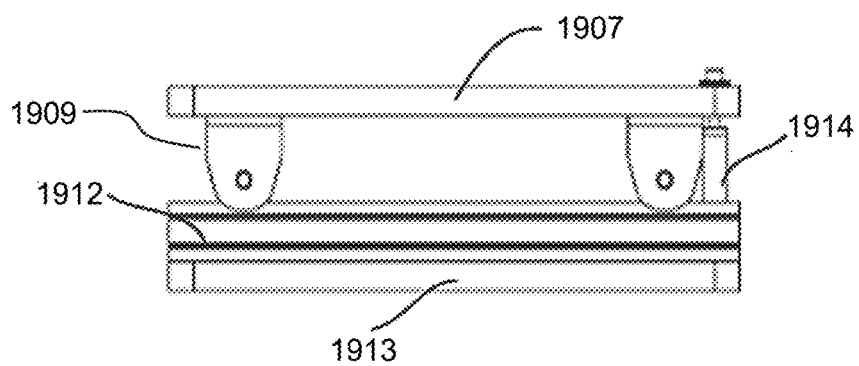
FIG. 19D illustrates a side view of an exemplary sliding device according to some embodiments of the present disclosure.
Figure 19E:
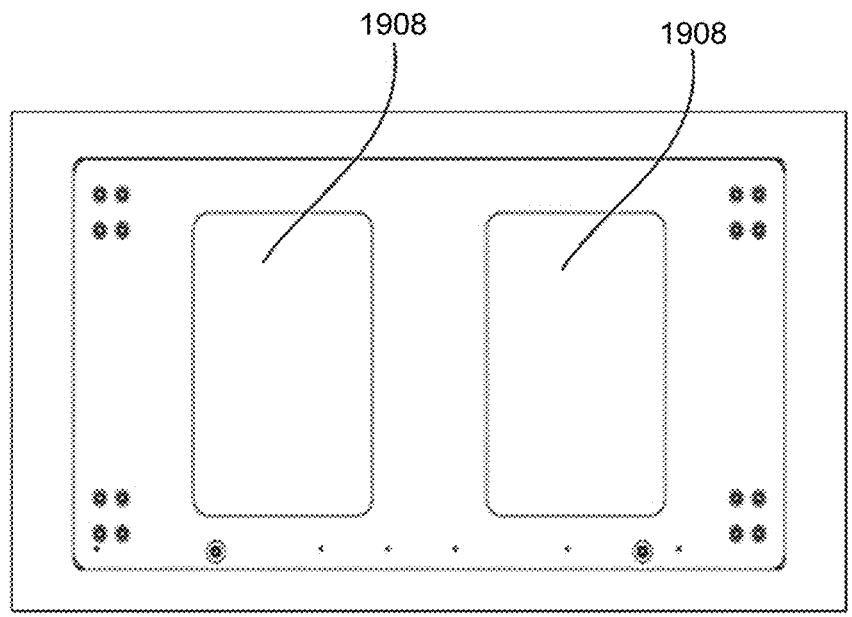
FIG. 19E illustrates a top view of an exemplary sliding device according to some embodiments of the present disclosure.

FIG. 19B illustrates a perspective view of an exemplary sliding device 1904 according to some embodiments of the present disclosure. FIG. 19C illustrates a front view of an exemplary sliding device 1904 according to some embodiments of the present disclosure. FIG. 19D illustrates a side view of an exemplary sliding device 1904 according to some embodiments of the present disclosure. FIG. 19E illustrates a top view of an exemplary sliding device 1904 according to some embodiments of the present disclosure. In some embodiments, the sliding device 1904 may include a supporting plate 1907, a sliding piece 1909, a guide component 1912, a baseplate (or baseboard) 1913, and a limit piece 1914.

The supporting plate 1907 may be configured to support the cooling device 1903. The supporting plate 1907 may directly contact or be in close proximity to one or more parts located at the bottom of the cooling device 1903 when the cooling device 1903 is placed on the supporting plate 1907. In some embodiments, the supporting plate 1907 may include one or more holes 1908 (see FIG. 19B, FIG. 19E, and FIG. 20A). In some embodiments, the holes 1908 may be through-holes. The holes 1908 may reduce the weight and/or the cost of the sliding device 1904, without reducing the rigidity or strength of the supporting plate 1907. In some embodiments, one or more holes may be configured on the baseplate 1913 to reduce the weight and/or the cost of the sliding device 1904.

In some embodiments, the sliding piece 1909 may be located underneath the supporting plate 1907. In some embodiments, the sliding piece 1909 may include a wheel assembly. The wheel assembly may include a wheel bracket 1910 and a wheel 1911 (see FIG. 19C). The wheel bracket 1910 may be fixedly connected to the supporting plate 1907. The wheel 1911 may be mounted on the wheel bracket 1910. Thus, the supporting plate 1907 may be connected with the wheel 1911 through the wheel bracket 1910. The supporting plate 1907 and the cooling device 1903 located on the supporting plate 1907 may slide when driven by the wheel 1911. In some embodiments, the sliding piece 1909 may include a sliding block, a sliding sheet, a sliding plate, or the like, or any combination thereof.

Figure 20A:
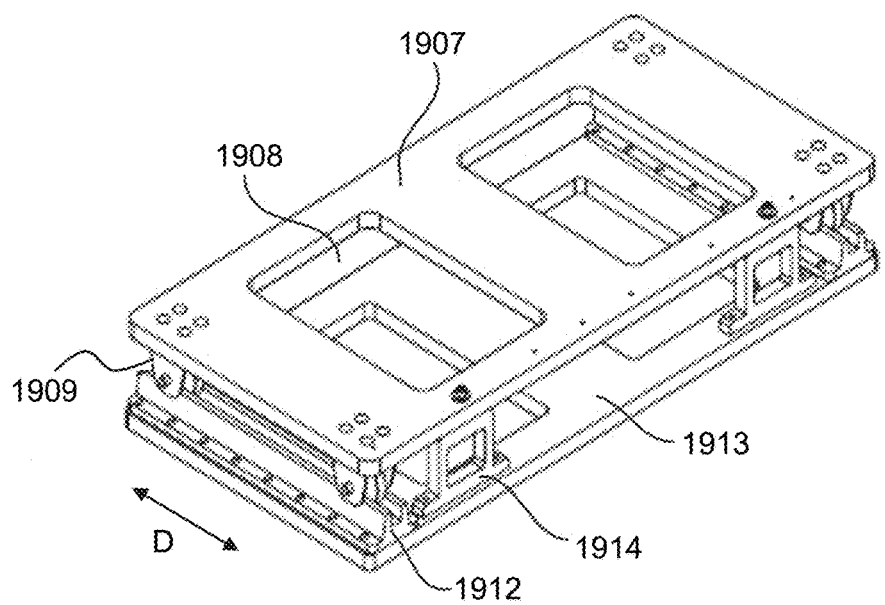
FIGS. 20A and 20B illustrates a perspective view and a front view of another exemplary sliding device according to some embodiments of the present disclosure.
Figure 20B:
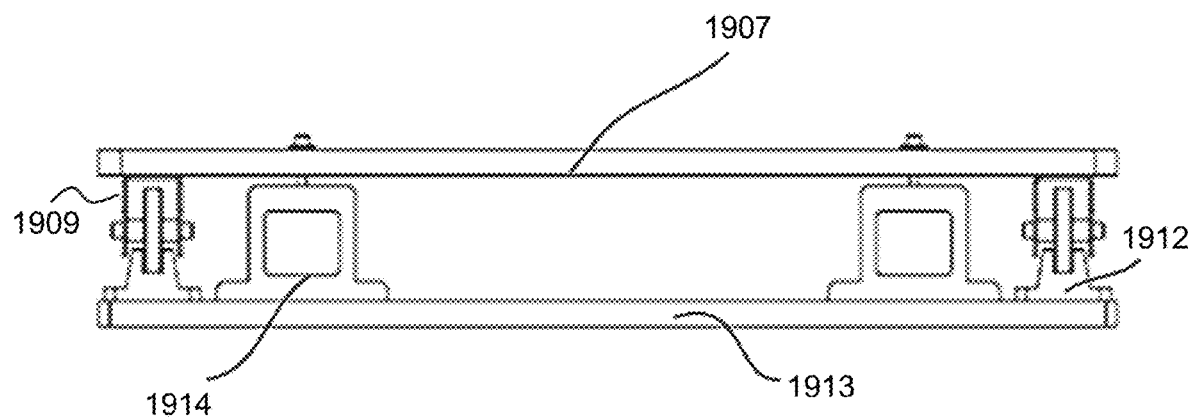

In some embodiments, the baseplate 1913 may be configured on the gantry base 1901. For instance, the baseplate 1913 may be fixed on the gantry base 1901 or be placed directly on the gantry base 1901. In some embodiments, the guide component 1912 supporting the sliding piece 1909 may in turn be supported on the baseplate 1913. In some embodiments, the guide component 1912 may include a sliding rail (also referred to as sliding guide rail), as shown in FIG. 19B. The sliding rail may include a linear sliding rail, a linear guide rail, or the like. The wheel 1911 may slide on the sliding rail, thereby driving the supporting plate 1907 and the cooling device 1903 located on the supporting plate 1907 to move. In some embodiments, the moving direction of the supporting plate 1907 may be indicated by the arrow D as illustrated in FIG. 19B. In some embodiments, one or more limit pieces 1914 may be configured on the baseplate 1913 to limit the position of the cooling device 1903. In some embodiments, the guide component 1912 may include one or more guide grooves configured on the baseplate 1913, as shown in FIG. 20A and FIG. 20B. In some embodiments, the gantry base 1901 may include a guide component configured to coordinate with the sliding piece of the sliding device, and the baseplate 1913 may be unnecessary. In some embodiments, the guide component may be mounted or formed on the gantry base 1901.

FIGS. 20A and 20B illustrates a perspective view and a front view of another exemplary sliding device 1904 according to some embodiments of the present disclosure. Considering that the space for accommodating the cooling device 1903 may be limited, the guide groove(s) (also referred to as the guide component 1912) supported on the baseplate 1913 may reduce the overall height of the sliding device 1904. The wheel 1911 may slide on the guide groove(s), thereby driving the supporting plate 1907 and the cooling device 1903 located on the supporting plate 1907 to move. In some embodiments, the moving direction of the supporting plate 1907 may be indicated by the arrow D as illustrated in FIG. 20A. In some embodiments, the guide component 1912 may include a guide groove formed on the baseboard 1913. This structure may further reduce the overall height of the sliding device 1904 so as to facilitate assembly of the cooling device 1903 in a relatively small space. The guide component 1912 may guide and limit the sliding path of the sliding piece 1909 such that the cooling device 1903 may be accurately slide to a predetermined position by the coordination of the guide component 1912 and the sliding piece 1909, and be aligned with the inlet chamber port 1905 and the return chamber port 1906.

The limit piece 1914 may be configured to limit the position of the cooling device 1903 in order to avoid the supporting plate 1907 and the cooling device 1903 located on the supporting plate 1907 to move beyond a certain position along a direction. In some embodiments, the limit piece 1914 may be fixed on the baseplate 1913. As illustrated in FIG. 20B, the height of the limit piece 1914 may be slightly lower than the vertical distance between the supporting plate 1907 and the baseplate 1913 defined by the height of the guide component 1912 and the height of the sliding piece 1909. In some embodiments, a first screw hole may be configured on an end face of the supporting plate 1907. A second screw hole corresponding to the first screw hole may be configured on an end face of the limit piece 1914. The sliding piece 1909 may drive the supporting plate 1907 and the cooling device 1903 located on the supporting plate 1907 to move to a predetermined position by the coordination of the sliding piece 1909 and the guide component 1912. Then the supporting plate 1907 and the limit piece 1914 may be fixed together using one or more screws and the screw holes located on the end face of the supporting plate 1907, and thus, the position of the cooling device 1903 may be fixed.

In some embodiments, the guide component 1912 and the limit piece 1914 may be supported on the baseplate 1913. Accordingly, both of the guide component 1912 and the limit piece 1914 are not directly mounted on the gantry base 1901, and an engineer or technician does not have to install the guide component 1912 and the limit piece 1914 within the relatively small space of the gantry (e.g., a space for accommodating the cooling device 1903 in a PET imaging device underneath the scanning channel). The installation of the guide component 1912 and the limit piece 1914 onto the baseplate 1913 may be performed in an open space outside the gantry (e.g., in a room where the imaging device is located), a space different from the space for accommodating the cooling device 1903 in a PET imaging device. Then the baseplate 1913 may be placed on the gantry base 1901. The cooling device 1903 may slide on the gantry base 1901 by the coordination of the sliding piece 1909 and the guide component 1912. Thus, the installation and disassembly of the cooling device 1903 may be facilitated. The guide component 1912 and the limit piece 1914 configured on the baseplate 1913 may guide the cooling device 1903 to slide accurately to a predetermined position and be fixed in the predetermined position.

Figure 21:
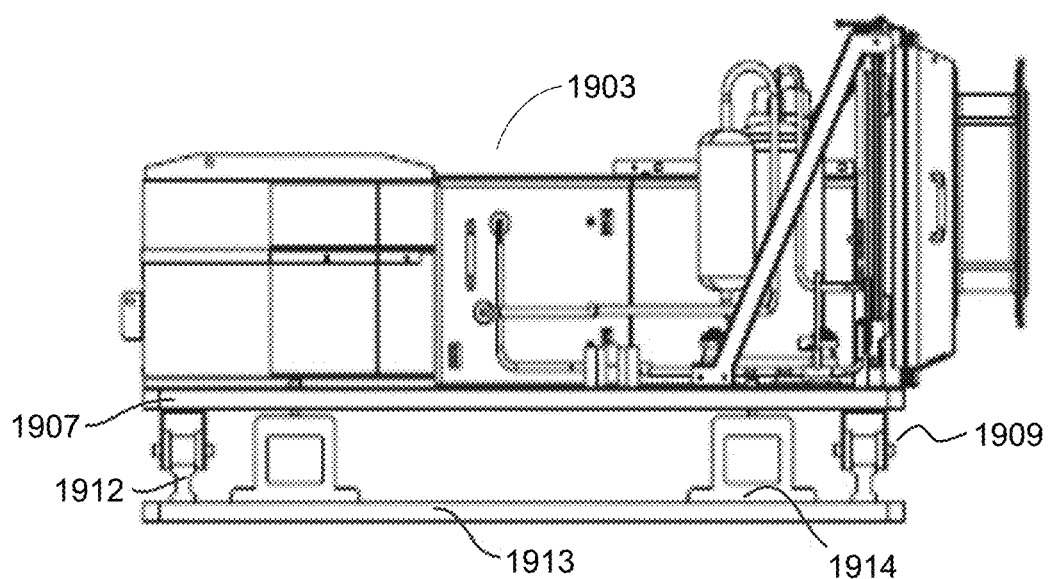
FIG. 21 illustrates a perspective view of an exemplary cooling device supported on an exemplary sliding device according to some embodiments of the present disclosure.

FIG. 21 illustrates a perspective view of an exemplary cooling device 1903 supported on an exemplary sliding device 1904 according to some embodiments of the present disclosure. In some embodiments, the sliding device 1904 may include the supporting plate 1907, the sliding piece(s) 1909, the guide component(s) 1912, the baseplate 1913, and the limit piece(s) 1914.

To install the cooling device 1903 on a gantry (e.g., a PET imaging device), the baseplate 1913 configured with the guide component(s) 1912 and the limit piece(s) 1914 may be pushed to a predetermined position on the gantry base 1901 firstly. The predetermined position may be a position where the cooling device 1903 may accurately align with the inlet chamber port 1905 and the return chamber port 1906. The cooling device 1903 may then be placed on the supporting plate 1907. The cooling device 1903 may be placed on the supporting plate 1907 directly or may be fixed on the supporting plate 1907 using screws. The supporting plate 1907 may slide on the guide component 1912 through the sliding piece 1909. The cooling device 1903 may slide to a predetermined position through the coordination of the sliding piece 1909 and the guide component 1912. The supporting plate 1907 and the limit piece(s) 1914 may be fixed together using screws. Thus, the cooling device 1903 may be installed on the gantry base 1901. Releasable fasteners (e.g., buckles) other than screws may be used.

To disassemble the cooling device 1903 from the gantry (e.g., a PET imaging device), the screws (or other releasable fasteners) connecting the supporting plate 1907 and the limit piece(s) 1914 may be released firstly. The cooling device 1903 supported on the supporting plate 1907 may be moved away from the inlet chamber port 1905 and the return chamber port 1906 by moving the supporting plate 1907. When the supporting plate 1907 is moved to a certain position, the cooling device 1903 may be removed from the supporting plate 1907.

It should be noted that the above description of the sliding device 1904 is merely provided for the purposes of illustration, and not intended to limit the scope of the present disclosure. For persons having ordinary skills in the art, multiple variations or modifications may be made under the teachings of the present disclosure. For example, the limit piece 1914 and the guide component 1912 may be unnecessary. As another example, the sliding device 1904 may have a self-locking function such that the supporting plate 1907 may not arbitrarily move. As still another example, the sliding device 1904 may automatically slide activated by pressing a button on the gantry. However, those variations and modifications do not depart from the scope of the present disclosure.

In some embodiments, a sliding device 1904 may include a supporting plate and a sliding piece. Before installing the cooling device 1903 on the gantry (e.g., a PET imaging device), the cooling device 1903 may be placed on the supporting plate firstly. The cooling device 1903 may then be pushed on the gantry base 1901 through the sliding device. The sliding device may have a locking function. If the sliding device slides to a predetermined position, the supporting plate may stop sliding using the locking function of the sliding piece. The predetermined position may be a position where the cooling device 1903 may be accurately aligned with the inlet chamber port 1905 and the return chamber port 1906 configured on the gantry.

In some embodiments, the sliding device 1904 may include a supporting plate, a sliding piece, and a guide component. To install the cooling device 1903 on a gantry (e.g., the PET imaging device), the guide component may be mounted on the gantry base 1901 firstly. The cooling device 1903 may then be placed on the supporting plate. The cooling device 1903 may slide to a predetermined position through the coordination of the sliding piece and the guide component by causing the supporting plate of the sliding piece to move. The guide component may include a sliding rail, a guide groove, or the like. The guide groove may be mounted on the gantry base 1901 or may be formed (e.g., by way of carving) in the gantry base 1901.

Figure 22A:
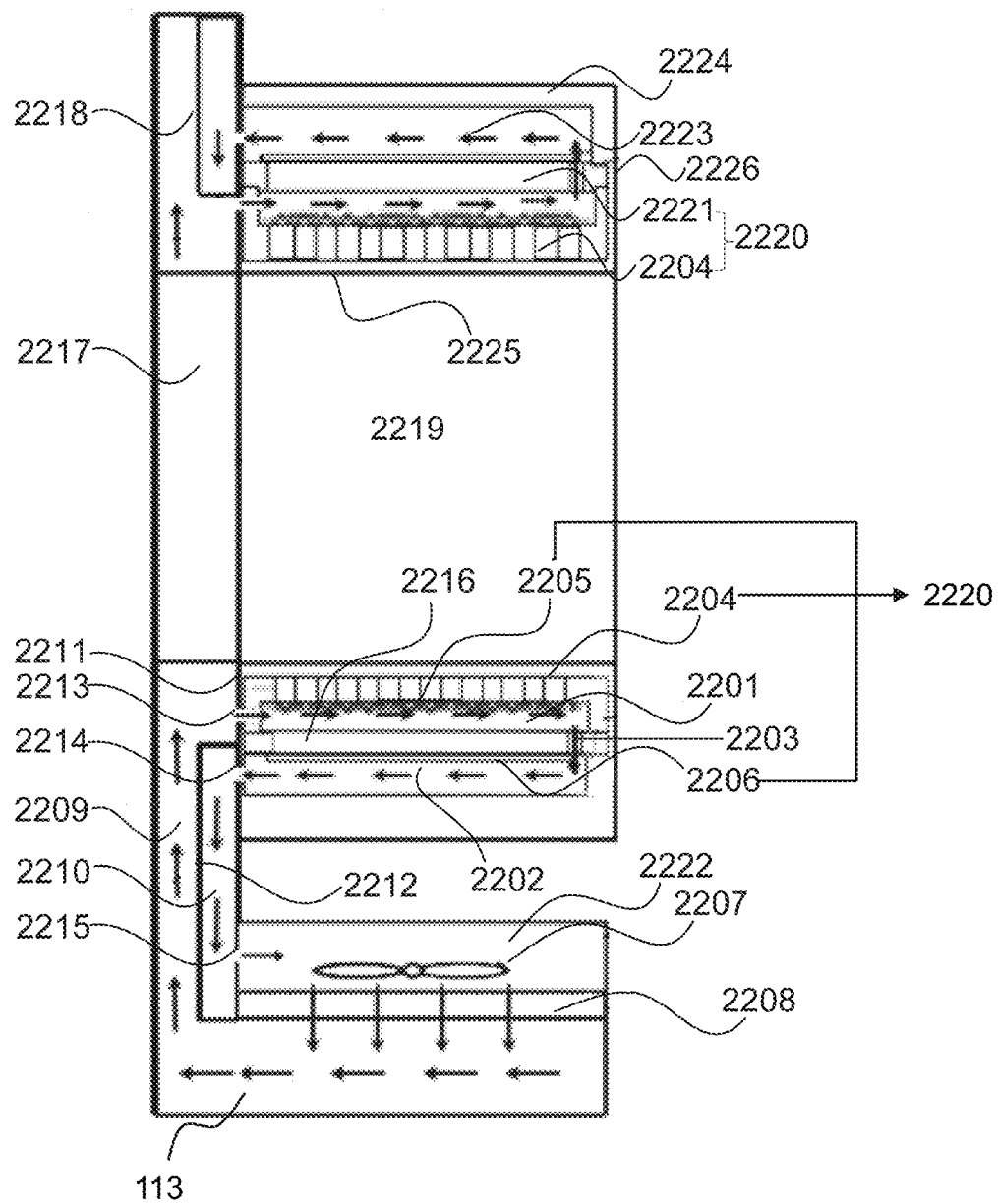
FIG. 22A illustrates a schematic diagram of an exemplary cooling assembly installed in an exemplary gantry according to some embodiments of the present disclosure.

FIG. 22A illustrates a schematic diagram of an exemplary cooling assembly 113 installed in an exemplary gantry according to some embodiments of the present disclosure. As illustrated in FIG. 22A, a PET imaging device may be used as an example for illustration purposes. The PET imaging device may include a gantry 2217, a detector cover 2224, one or more detector modules 2220, a scanning channel 2219, and a cooling assembly 113. The detector modules 2220 may be mounted on the gantry 2217 along a peripheral edge of the scanning channel 2219. In some embodiments, the orientation of the detector modules 2220 may be parallel (or substantially parallel) to the axial direction of the scanning channel 2219 and perpendicular (or substantially perpendicular) to a front cover plate of the gantry 2217. In some embodiments, the detector cover 2224 may shield against an electromagnetic field and/or a radiation ray (e.g., an X-ray radiation of a CT device). In some embodiments, the detector cover 2224 may protect the detector module 2220 from electromagnetic interferences. In some embodiments, the cooling assembly 113 may include one or more chilling chambers (e.g., the chilling chamber 2223) surrounding the detector modules 2220, a refrigerator 2222, an inlet chamber 2209, and a return chamber 2210 connecting the chilling chamber(s) and the refrigerator 2222. In some embodiments, the inlet chamber 2209 and the return chamber 2210 may be adjacent to each other. In some embodiments, the inlet chamber 2209 and the return chamber 2210 may be integrated on a main gantry. In some embodiments, a thermal insulation layer may be arranged on a common plane (or referred to as a coplane) the inlet chamber 2209 and the return chamber 2210 share. The detector module 2220 may be fixed on the coplane 2227. An air intake 2213 and an air outlet 2214 may be formed on the coplane 2227. In some embodiments, a thermal insulation layer may be configured on the wall of the chilling chamber 2223 in order to reduce undesired heat exchange between the cooling medium in the chilling chamber 2223 and the air outside the cover plate 2226 (e.g., a circular cover plate).

As illustrated in FIG. 22A, an air cooling assembly may be taken as an example. In some embodiments, the cooling assembly 113 may include an air blower 2207, a heat exchanger 2208 located adjacent to the air blower 2207, an inlet chamber 2209 in fluid communication with the heat exchanger 2208, a return chamber 2210 separated from the inlet chamber 2209. The cooling assembly 113 may include a compressor (not shown). The compressor may be located in a cooling device (e.g., the cooling device 1903) of the cooling assembly 113. In some embodiments, the air blower 2207 and the heat exchanger 2208 may be referred to as a refrigerator 2222. The inlet chamber 2209 and the return chamber 2210 may also be referred to as air chambers. The arrows illustrated in the diagram may indicate the flow direction of a cooling medium (e.g., air).

A detector module 2220 may include one or more crystal units 2204 and a circuit board unit 2221. The circuit board unit 2221 may include a photomultiplier plate 2205 optically coupled to the crystal units 2204 and a front-end electronics circuit board 2206 electrically coupled to the photomultiplier plate 2205. The photomultiplier plate 2205 may be located on a side of the crystal unit 2204 facing a connection assembly 2216. The photomultiplier plate 2205 may be fixed on both ends of the connection assembly 2216 along a longitudinal direction of the connection assembly 2216.

In some embodiments, the detector module 2220 may be fixed to the gantry 2217 through the connection assembly 2216. In some embodiments, the detector module 2220 may include a hollow chamber housing one or more detector units of the detector module 2220. The hollow chamber may further include a first chamber 2201 and a second chamber 2202. The first chamber 2201 and the second chamber 2202 may be separated by the connection assembly 2216. The first chamber 2201 may be formed between the photomultiplier plate 2205 and the connection assembly 2216. The front-end electronics circuit board 2206 may be located on a back side of the connection assembly 2216 away from the photomultiplier plate 2205. The second chamber 2202 may be formed between the front-end electronics circuit board 2206 and the connection assembly 2216. In some embodiments, a hole 2203 may be formed on an end of the connection assembly 2216 along an axial direction of the scanning channel 2219 away from the cooling assembly 113. The cooling medium may flow from the first chamber 2201 to the second chamber 2202 (or vice versa) through the hole 2203.

The air chamber(s) may be surrounded by one or more baffles. In some embodiments, a baffle 2211 may separate the air chamber from a detector module 2220. A clapboard 2212 may be configured in the air chamber and connected with the baffle 2211. The clapboard 2212 may divide the air chamber into an inlet chamber 2209 and a return chamber 2210. In some embodiments, the inlet chamber 2209 and the return chamber 2210 may be separated by the clapboard 2212 and/or a common plane 2218 such that the inlet chamber 2209 and the return chamber 2210 are not in fluid communication with each other except through the passageway formed by the first chamber 2201 and the second chamber 2202. In some embodiments, an air intake 2213 and an air outlet 2214 may be formed on the baffle 2211. The inlet chamber 2209 may be connected or in fluid communication with the first chamber 2201 through the air intake 2213. The return chamber 2210 may be connected or in fluid communication with the second chamber 2202 through the air outlet 2214.

The air blower 2207 may drive the cooling medium to spread and/or circulate in the air chamber(s). The air blower 2207 may regulate the flow rate of the cooling medium. The air blower 2207 may be a fan or a blower. In some embodiments, the flow rate of the cooling medium may be regulated through the variation of the rotation speed of the air blower 2207. The heat exchanger 2208 may cool the cooling medium. The heat exchanger 2208 may be a shell and tube heat exchanger, a pillow plate heat exchanger, a fluid heat exchanger, a dynamic scraped surface heat exchanger, a phase-change heat exchanger, or a direct contact heat exchanger, or the like, or any combination thereof. In some embodiments, the heat exchanger 2208 may use a cryogen and/or a refrigerant to cool the cooling medium. For example, the heat exchanger 2208 may be an evaporator; the evaporator may include one or more conduits with a cryogen.

In some embodiments, the detector module 2220 may be a target location to be cooled. In some embodiments, the cooling medium may be blew to the inlet chamber 2209 by the air blower 2207. The cooling medium may then reach the first chamber 2201 via the air intake 2213. The cooling medium may cool down the crystal unit 2204 and the photomultiplier plate 2205 in the first chamber 2201. The cooling medium may then flow into the second chamber 2202 through the hole 2203 on the connection assembly 2216. The cooling medium may cool down the front-end electronics circuit board 2206 in the second chamber 2202. The cooling medium may flow into the return chamber 2210 through the air outlet 2214. The cooling medium may flow back to an air supply chamber housing the air blower 2207 through a return chamber port 2215. Then, the cooling medium may be cooled by the heat exchanger 2208 for reuse.

In some embodiments, a cover plate 2226 (e.g., a circular cover plate) may be mounted on an end of the detector modules 2220 away from the front cover plate of the gantry 2217. A chilling chamber 2223 may include a first chamber (e.g., the first chamber 2201) and/or a second chamber (e.g., the second chamber 2202). The chilling chamber 2223 may surround the detector module 2220. The chilling chamber 2223 may be formed by a sidewall of the gantry 2217, the cover plate 2226, an inner sidewall of the scanning channel 2225, and a back cover plate (not shown). In some embodiments, the chilling chamber 2223 housing the detector modules 2220 may be configured as a sealed space (also refer to as a confined chamber) in order to improve the cooling efficiency of the cooling assembly 113. In some embodiments, a chilling chamber (e.g., the chilling chamber 2223) may include one or more clapboards configured to divide the chilling chamber into a plurality of sub chambers according to the number of the plurality of detector modules. In some embodiments, a sub chamber may include an air intake of an inlet chamber (e.g., the inlet chamber 2209) and an air outlet of a return chamber (e.g., the return chamber 2210).

Figure 22B:
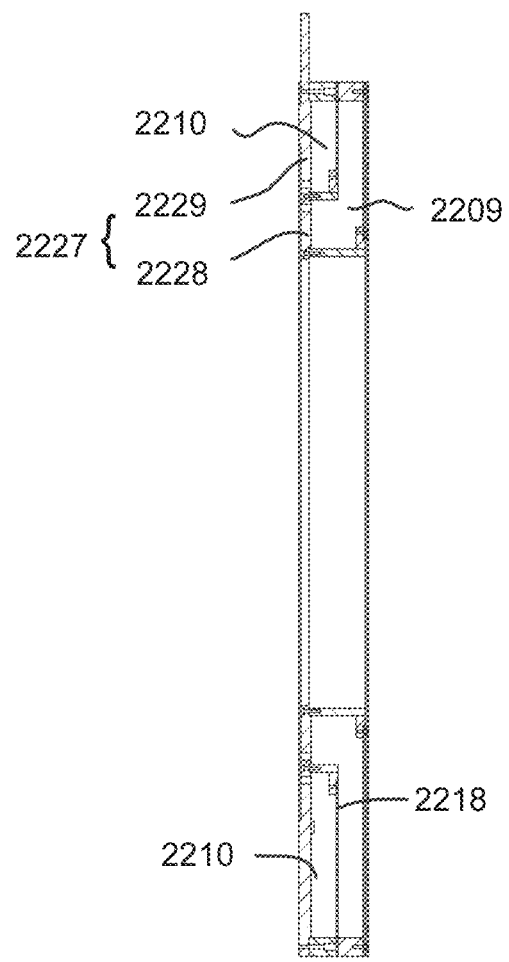
FIG. 22B illustrates a schematic diagram of an exemplary cooling assembly installed in an exemplary main mounting plate according to some embodiments of the present disclosure.

FIG. 22B illustrates a schematic diagram of an exemplary cooling assembly 113 installed in an exemplary main mounting plate according to some embodiments of the present disclosure. In some embodiments, a thermal insulation layer may be configured on a common plane 2218 of an inlet chamber 2209 and a return chamber. The thermal insulation layer may prevent undesired heat exchange between the cooling medium in the inlet chamber 2209 and that in the return chamber 2210. In some embodiments, the temperature difference between the inlet chamber 2209 and the return chamber 2210 may be about 5° C.). The thermal insulation layer may include insulated cotton, cystosepiment, or the like, or any combination thereof. In some embodiments, a thermal insulation layer may be configured on a plane other than the common plane of the inlet chamber 2209 and the return chamber 2210 in order to reduce undesired heat absorption of the cooling medium in the inlet chamber 2209. For example, a plane other than the common plane between the inlet chamber 2209 and the return chamber 2210 may include a thermal insulation layer. As another example, a sidewall of the chilling chamber(s) may include a thermal insulation layer.

It should be noted that the above description of the diagrams in FIG. 22A and FIG. 22B is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, holes or conduits may be formed on a sidewall of the air chamber(s) to connect the air chamber(s) with other cooling medium passage outside the air chamber(s). As another example, the air blower 2207 and the heat exchanger 2208 may be placed in the air chamber(s). As still another example, the air blower 2207 and the heat exchanger 2208 may be placed outside of the air chamber(s) (e.g., at the bottom of the gantry), and an additional chamber may be formed to connect the air blower 2207 and/or the heat exchanger 2208 with the air chamber(s). As a further example, the heat exchanger 2208 may be unnecessary; instead, an additional inlet may be configured to introduce a cooled cooling medium into the air chamber(s), and an additional outlet may be configured to guide an exhausted cooling medium to flow out from the air chamber(s). As a still further example, the inlet chamber 2209 and the return chamber 2210 may be separated by the clapboard 2212, the common plane 2218, and/or the baffle 2211. As a still further example, the inlet chamber 2209 and the return cavity 2210 may be separated by any other clapboard, plate, and/or baffle (not shown) that may achieve a similar function.

Figure 23A:
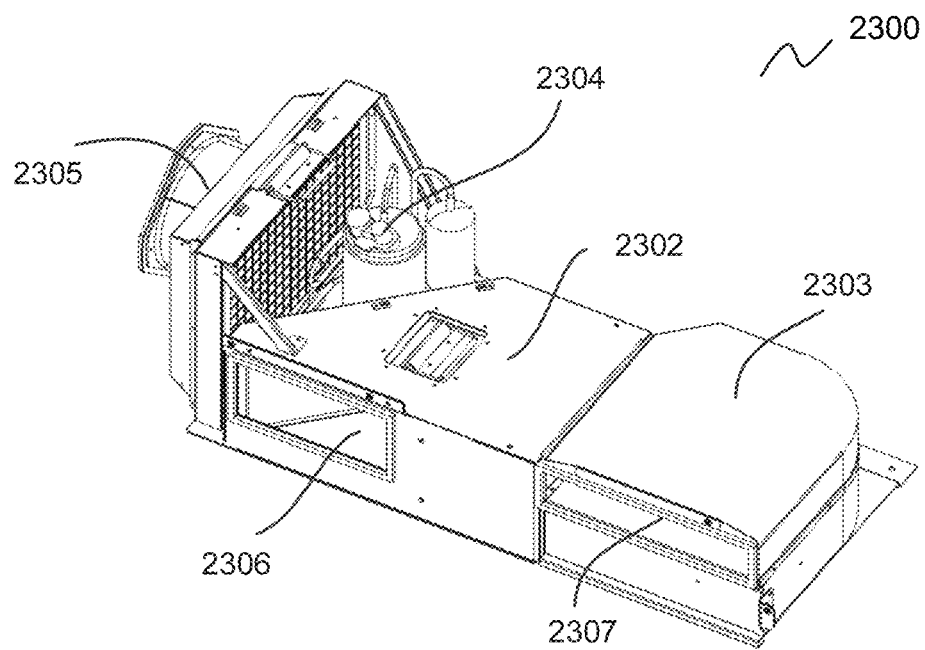
FIG. 23A illustrates an exemplary cooling device according to some embodiments of the present disclosure.
Figure 23B:
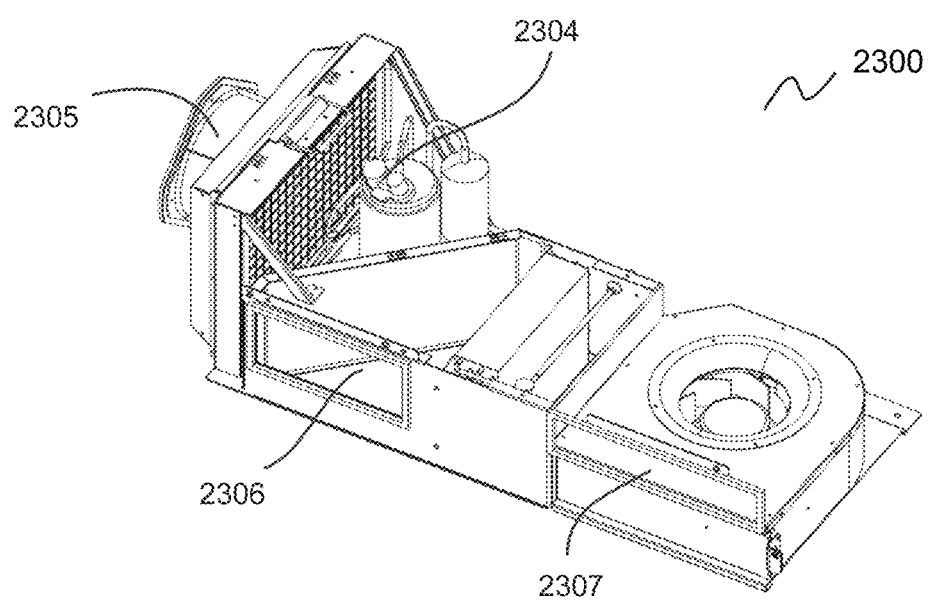
FIG. 23B illustrates an internal structure of the exemplary cooling device shown in FIG. 23A according to some embodiments of the present disclosure.

FIG. 23A illustrates an exemplary cooling device 2300 according to some embodiments of the present disclosure. FIG. 23B illustrates an internal structure of the exemplary cooling device 2300 shown in FIG. 23A according to some embodiments of the present disclosure. The cooling device 2300 may include a compressor 2304, a fan 2305, a compressor chamber 2302, and an air supply chamber 2303. The air supply chamber 2303 may include an air outlet 2307 of the cooling device 2300 corresponding to an inlet chamber port (e.g., the inlet chamber port 620, the inlet chamber port 1905). The compressor chamber 2302 may include an air intake 2306 of the cooling device 2300 corresponding to a return chamber port (e.g., the return chamber port 622, the return chamber port 1906). In some embodiments, one or more thermal insulation layers may be installed on the walls of the compressor chamber 2302 and/or the air supply chamber 2303.

In some embodiments, the cooling device 2300 and one or more chilling chambers (e.g., the chilling chamber 2223) may be located on the same side of a gantry. In some embodiments, the cooling device 2300 may be located below the chilling chamber(s) (see FIG. 22A). In some embodiments, the cooling device 2300 may be located on a left side, a right side, a front side, or a back side of the chilling chambers. In some embodiments, the cooling device 2300 may be located on top of the chilling chambers. The location of the cooling device 2300 relative to the chilling chamber(s) is not limited to those exemplified above in the present disclosure.

In some embodiments, an inlet chamber (e.g., the inlet chamber 2209) and a return chamber (e.g., the return chamber 2210) may be arranged adjacent to each other between the cooling device 2300 and the chilling chamber(s). In some embodiments, the inlet chamber and the return chamber may be integrated on a gantry or a main mounting plate of the gantry. In some embodiments, the inlet chamber port of the inlet chamber in fluid communication with a refrigerator (or cooler) and the return chamber port of the return chamber in fluid communication with the refrigerator (or cooler) are formed on a coplane facing the detector assembly 112. In some embodiments, the cooler may include a compressor chamber or an air supply chamber, and a sidewall of the compressor chamber or the air supply chamber may include a thermal insulation layer. The cooling medium cooled by the cooling device 2300 may flow into the chilling chamber(s) through the inlet chamber. Then the cooling medium may absorb heat from one or more detector modules (e.g., the detector module 2220). The exhausted cooling medium may flow back to the cooling device 2300 through the return chamber and be cooled for reuse. In some embodiments, the inlet chamber and the return chamber may form a coplane (e.g., the coplane 2227). The detector modules, a circular cover plate (e.g., the circular cover plate 2226), and the cooling device 2300 may be arranged on the coplane 2227. Thus, the assembly and disassembly of the gantry may be facilitated.

Figure 24A:
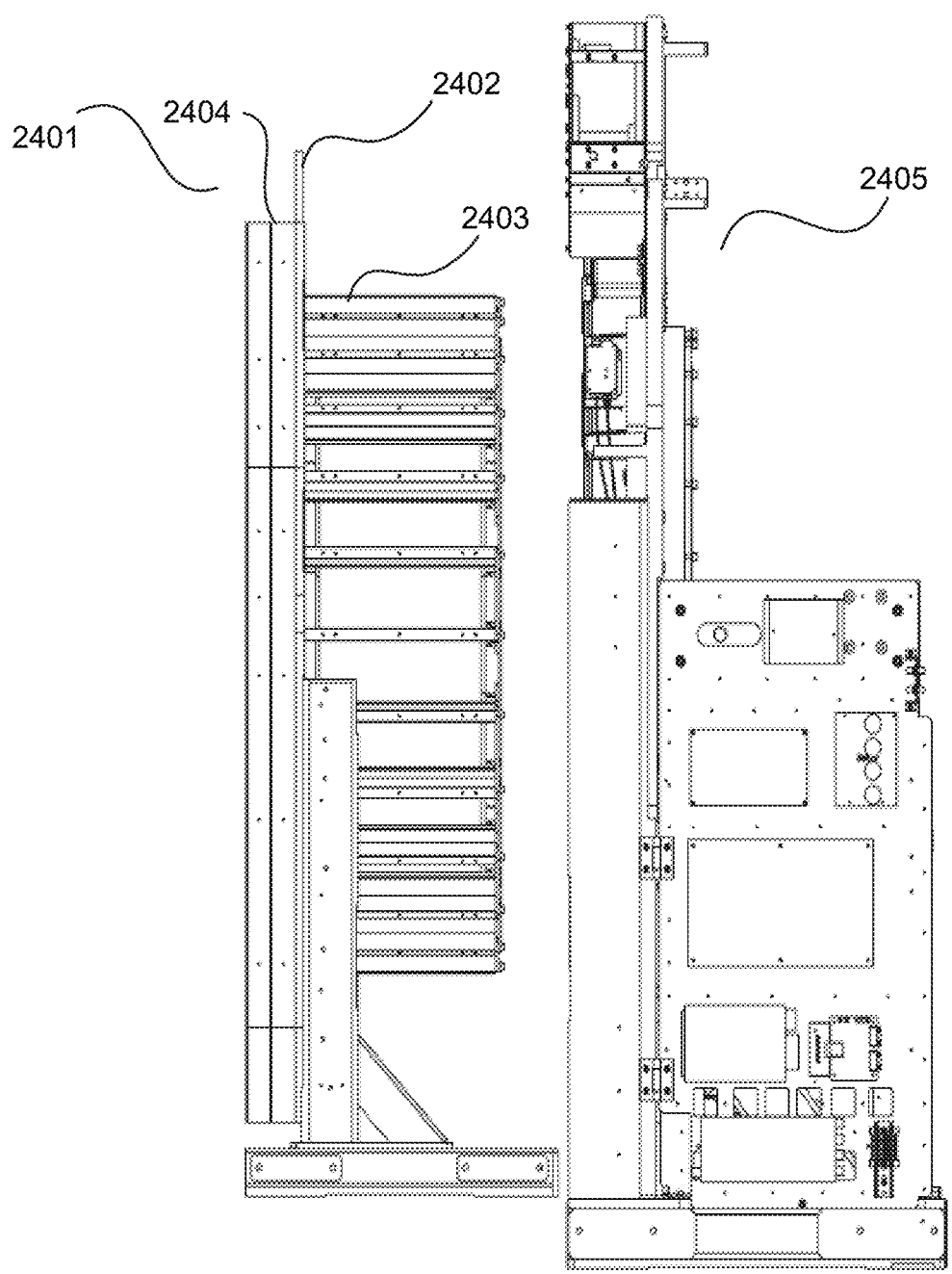
FIG. 24A illustrates an exemplary PET-CT imaging device according to some embodiments of the present disclosure.

FIG. 24A illustrates an exemplary PET-CT imaging device 2400 according to some embodiments of the present disclosure. The PET-CT imaging device 2400 may include a PET imaging device 2401 and a CT imaging device 2405. In some embodiments, the PET imaging device 2401 and the CT imaging device 2405 may be arranged side by side in an axial direction of a scanning channel. The PET imaging device 2401 may have a PET scanning channel. The CT imaging device 2405 may have a CT scanning channel. The PET scanning channel and the CT scanning channel may be configured for accommodating an object. In some embodiments, the PET scanning channel and the CT scanning channel may be coaxially arranged.

The PET imaging device 2401 may include a gantry 2402, a detector assembly configured on the gantry 2402, and a cooling assembly 2404 configured to cool the detector assembly. In some embodiments, the detector assembly may include one or more detector modules 2403 arranged circumferentially along the peripheral direction of the PET scanning channel. The gantry 2402 may support the detector assembly and the cooling assembly 2404 and form the PET scanning channel.

In some embodiments, the cooling assembly 2404 may be distributed on one or more sides of the detector assembly except for a side of the detector assembly facing the CT imaging device 2405. For example, as shown in FIG. 24A, the cooling assembly 2404 may be distributed on a back side, a left side, a right side, an upper side, or a lower side (or any combination thereof) of the detector assembly and are not distributed on a first side of the detector assembly. The first side may refer to the side of the detector assembly facing the CT imaging device 2405. The configuration of the cooling assembly 2404 may reduce a distance between a CT scanning plane of the CT imaging device 2405 and a PET scanning plane of the PET imaging device 2401. Thus, the structure of the PET-CT imaging device 2400 may be more compact. A compact structure of the PET-CT imaging device 2400 may shorten a scanning time and reduce a radiation dose to which the object is exposed in a scanning process. In some embodiments, a table (not shown) may be placed at one end of the PET-CT imaging device 2400 close to the CT imaging device 2405. In a scanning process, the table supporting an object may be moved to the CT scanning plane and then the PET scanning plane. With a compact structure of the PET-CT imaging device 2400, the distance that the table top needs to extend may be reduced, and the deformation of the table top (e.g., a table top with a cantilever structure) due to the weight of the object and/or the weight of the table top that extends out may be reduced. Thus, the accuracy of scanning may be improved. In some embodiments, the cooling assembly 2404 may have the configuration of the cooling assembly 113 illustrated in FIGS. 22A through 23B.

Figure 24B:
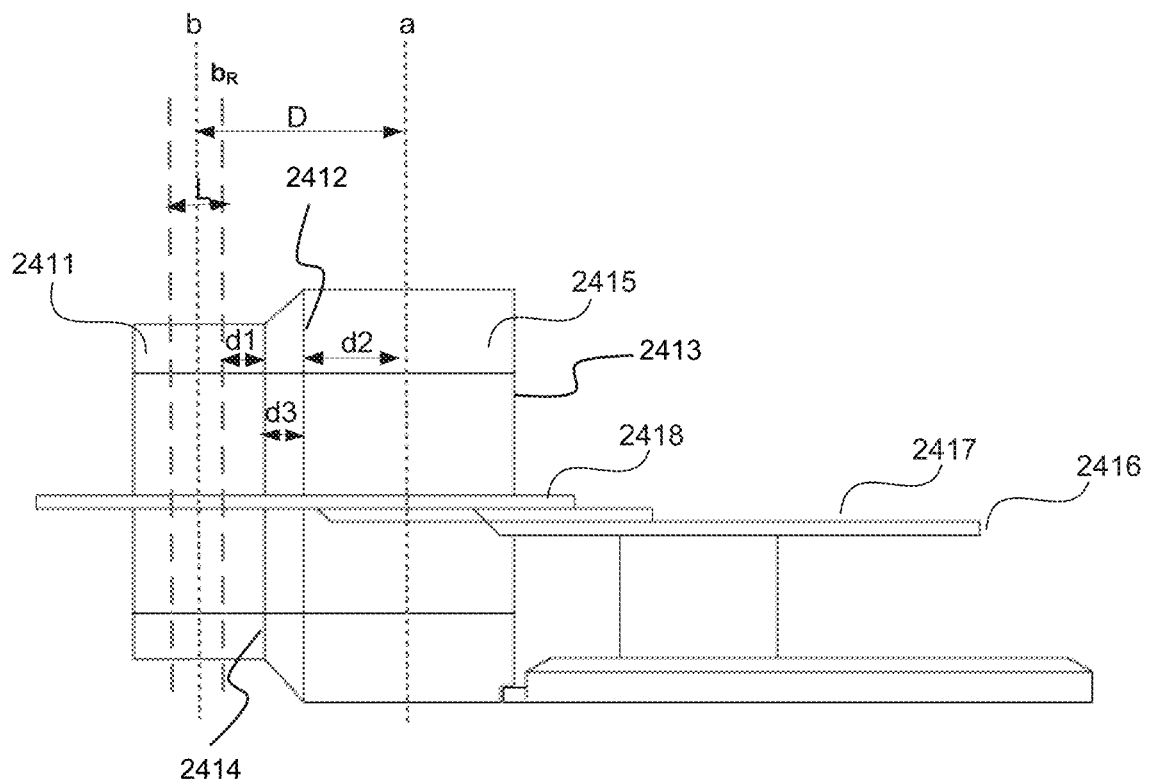
FIG. 24B illustrates an exemplary PET-CT imaging device according to some embodiments of the present disclosure.

FIG. 24B illustrates an exemplary PET-CT imaging device 2410 according to some embodiments of the present disclosure. The PET-CT imaging device 2410 may be substantially similar to the PET-CT imaging device 2400. The PET-CT imaging device 2410 may include a PET imaging device 2411 and a CT imaging device 2415. In some embodiments, a table 2416 may be configured on an end of the PET-CT imaging device 2410 close to the CT imaging device 2415. The table 2416 may include a table base 2417 and a table top 2418. The table top 2418 may be slidably connected to the table base 2417. The table top 2418 may support an object and send the object to a CT scanning channel of the CT imaging device 2415. A scan region of the object may be located on a CT scanning plane a. In some embodiments, the CT scanning plane a may pass through a CT tube and a midpoint in an axial direction of the CT scanning channel.

After the CT scanning is completed, the table top 2418 may continue to move into a PET scanning channel of the PET imaging device 2411 to a PET scanning plane b. The PET scanning plane b may be a transverse plane that passes through the midpoint in an axial direction of the PET scanning channel. The distance between the CT scanning plane a and the PET scanning plane b may affect the PET-CT scanning time and the radiation dose to which an object is exposed.

In some embodiments, the distance between the CT scanning plane a and a first end face 2413 of the CT imaging device 2415 along the axial direction of the CT scanning channel may be less than 350 mm. The first end face 2413 may be close to the table base 2417 and away from the PET imaging device 2411. The distance may also refer to the distance between the CT tube and the first end face 2413 of the CT imaging device 2415. In some embodiments, the distance may be within the range of 300 millimeters to 330 millimeters.

The PET imaging device 2411 may have a number of detector rings (e.g., 32 rings, 88 rings, 96 rings, 112 rings, etc.). The PET rings of the PET imaging device 2411 may relate to the number of the detector crystals distributed in the axial direction of the PET scanning channel. PET imaging devices configured with different number of detector rings may have different axial fields of view (AFOV). As shown in FIG. 24B, the distance between the CT scanning plane a of the CT imaging device 2415 and the PET scanning plane b of the PET imaging device 2411 may be designated as D. The length of the detector assembly in the axial direction along the PET scanning channel may be designated as L. The distance between a transverse plane $b_R$ of the detector assembly close to the CT imaging device 2415 and a third end face 2414 of the PET imaging device 2411 along the axial direction of the PET scanning channel may be designated as d1. The detector assembly may have a first side (also referred to as the transverse plane $b_R$) and a second side along an axial direction of the PET scanning channel. The first side may be closer to the CT imaging device 2415 than the second side. The distance between the first side of the detector assembly and the front side of the PET imaging device 2411 along the axial direction of the scanning channel may be designated as d1. The third end face 2414 (or a front side) of the PET imaging device 2411 may be close to the CT imaging device 2415. The distance between the CT scanning plane a and a second end face 2412 of the CT imaging device 2415 in the axial direction along the CT scanning channel may be designated as d2. The second end face 2412 of the CT imaging device 2415 may be close to the PET imaging device 2411. The distance between the second end face 2412 of the CT imaging device 2415 and the third end face 2414 of the PET imaging device 2411 may be designated as d3. In some embodiments, d3 may be equal to or larger than 0. In some embodiments, the distance D between the PET scanning plane b and the CT scanning plane a may be (L/2+d1+d2+d3). In some embodiments, d1 may be equal to or less than 170 millimeters. In some embodiments, d1 may be equal to or less than 150 millimeters. In some embodiments, d1 may be equal to or less than 105 millimeters or 90 millimeters. Using the structure of the first PET-CT imaging device 2400 described in FIG. 24A, d1 may be effectively reduced due to its compact structure, and thus, the distance between the PET scanning plane b and the CT scanning plane a may be reduced correspondingly. In some embodiments, the CT imaging device 2415 may have a first end surface (also referred to as the first end face 2413) and a second end surface (also referred to as the second end face 2412) along an axial direction of the CT scanning channel. The first end surface is farther from the PET imaging device 2411 than the second end surface. The CT imaging device 2415 may include an X-ray tube. The distance between the X-ray tube and the first end surface of the CT imaging device 2415 along an axial direction of the CT scanning channel may be equal to or less than 350 millimeters.

In some embodiments, the PET imaging device 2411 may have 88 detector rings. Accordingly, d1 may be in a range of 160 millimeters to 170 millimeters, and D may be in a range of 500 millimeters to 600 millimeters. In some embodiments, the PET imaging device 2411 may have 96 detector rings. Accordingly, d1 may be in a range of 150 millimeters to 160 millimeters, and D may be in a range of 600 millimeters to 700 millimeters. In some embodiments, the PET imaging device 2411 may have 112 detector rings. Accordingly, d1 may be in a range of 130 millimeters to 150 millimeters, and D may be in a range of 550 millimeters to 650 millimeters.

In some embodiments, an imaging system (e.g., a PET-CT imaging system) may include a first device (e.g., a CT imaging device) and/or a second device (e.g., a PET imaging device). The first device may include a first scanning channel. The second device may include a second scanning channel connected to the first scanning channel. The second device may include a heat generating component facing a first side of the second device, wherein the first side of the second device (e.g., the third end face 2414) may face the first device. The heat generating component may include one or more detector modules. The second device may include a cooling assembly configured to cool the heat generating component, wherein the cooling assembly may be located at a second side (e.g., a back side, a left side, a right side, an upper side, or a lower side, or any combination thereof) of the second device, and the second side of the second device may be different from the first side of the second device.

It should be noted that the above description of the PET-CT imaging device 2400 and the PET-CT imaging device 2410 is merely provided for the purposes of illustration, and not intended to limit the scope of the present disclosure. For persons having ordinary skills in the art, multiple variations and modifications may be made under the teachings of the present disclosure. In some embodiments, a PET imaging device may be combined with another type of medical imaging device. For example, a PET imaging device may be in combination with an MR device to form a PET/MR device. As another example, a PET imaging device may be in combination with an X-ray device to form a PET/X-ray device. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. An imaging system, comprising:
a detector assembly including a plurality of detector modules and a detector support configured to support the plurality of detector modules; and
a gantry assembly including a main gantry, a front cover plate, and a position adjustment device, wherein
the detector assembly is mounted on the main gantry; and
the position adjustment device is configured to adjust a position of the front cover plate relative to the main gantry, and the position adjustment device includes:
one or more bulged ends;
one or more sliding holes configured on the bulged ends, the one or more bulged ends and the one or more sliding holes being configured to connect the position adjustment device to the main gantry.

2. The system of claim 1, wherein the detector support includes a plurality of guide units configured to facilitate mounting of the plurality of detector modules and limit movement of the plurality of detector modules.

3. The system of claim 2, wherein the at least one of the plurality of guide units includes a limit piece configured to limit a movement of at least one of the plurality of detector modules.

4. The system of claim 3, wherein the at least one of the plurality of guide units includes a guide plate arranged along an axial direction of the scanning channel, the guide plate includes a guide rail, and the at least one of the plurality of detector modules includes at least one guide piece complementary to the guide rail.

5. The system of claim 3, wherein the plurality of guide units include a plurality of guide plates distributed along the scanning channel circumferentially, at least one of the plurality of guide plates includes a limit sheet, and the at least one of the plurality of detector modules includes a limit block corresponding to the limit sheet.

6. The system of claim 3, wherein the plurality of guide units include a plurality of guide columns, and the at least one of the plurality of detector modules includes a guide hole corresponding to one of the plurality of guide columns.

7. The system of claim 1, further comprising a detector cover configured to cover the detector support.

8. The system of claim 7, wherein the detector cover includes a plurality of first-type sub detector covers fixed on the main gantry and a plurality of second-type sub detector covers held in place by the plurality of first-type sub detector covers.

9. The system of claim 1, wherein the position adjustment device includes:
a first moving piece mechanically connected to the front cover plate;
a first adjustment piece mechanically connected to the first moving piece and configured to move the first moving piece along a first direction, wherein the movement of the first moving piece drives the front cover plate to move.

10. The system of claim 9, further comprising a fixed pin fixed on the front cover plate, wherein the first moving piece includes a fixed hole, and the fixed pin is fixed on the first moving piece through the fixed hole.

11. The system of claim 10, wherein the fixed pin and the first moving piece is an integral piece.

12. The system of claim 9, wherein a housing of the position adjustment device includes one or more adjustment holes configured to provide passage space for a tool to access and move the first adjustment piece along the first direction.

13. The system of claim 9, wherein the first adjustment piece includes a sliding rail extending along the first direction for the first moving piece to slide along.

14. The system of claim 9, the position adjustment device further includes:
a second moving piece mechanically connected to the first moving piece;
a second adjustment piece mechanically connected to the second moving piece and configured to move the second moving piece along a second direction, wherein the movement of the second moving piece drives the first moving piece to move.

15. The system of claim 14, wherein the second moving piece includes a first sliding cavity configured to allow the first moving piece to move along the first direction.

16. The system of claim 14, wherein a housing of the position adjustment device includes a second sliding cavity configured to allow the second moving piece to move along the second direction.

17. The system of claim 14, wherein the first adjustment piece includes a screw engaged in the second moving piece, and the first moving piece is caused to move along the first direction by adjusting the screw.

18. The system of claim 14, wherein the position adjustment device further includes a first fastener configured to hold the first adjustment piece in place in the second moving piece and prevent the first adjustment piece from falling out of the second moving piece.

19. The system of claim 14, wherein the position adjustment device further includes a second fastener configured to hold the second adjustment piece in place in a housing of the position adjustment device and prevent the second adjustment piece from falling out of the housing.

\* \* \* \* \*